US007662384B2

(12) United States Patent
Ramakrishnan et al.

(10) Patent No.: US 7,662,384 B2
(45) Date of Patent: Feb. 16, 2010

(54) USE OF ANTI-α5β1 ANTIBODIES TO INHIBIT CANCER CELL PROLIFERATION

(75) Inventors: Vanitha Ramakrishnan, Belmont, CA (US); Vinay Bhaskar, San Francisco, CA (US); Sun Ho, Fremont, CA (US); Richard Murray, Cupertino, CA (US); Debbie Law, San Francisco, CA (US)

(73) Assignee: Facet Biotech Corporation, Redwood City, CA (US)

( * ) Notice: Subject to any disclaimer, the term of this patent is extended or adjusted under 35 U.S.C. 154(b) by 282 days.

(21) Appl. No.: 11/090,331

(22) Filed: Mar. 24, 2005

(65) Prior Publication Data

US 2005/0260210 A1 Nov. 24, 2005

Related U.S. Application Data

(60) Provisional application No. 60/556,421, filed on Mar. 24, 2004, provisional application No. 60/556,442, filed on Mar. 24, 2004, provisional application No. 60/625,049, filed on Nov. 3, 2004, provisional application No. 60/651,098, filed on Feb. 7, 2005, provisional application No. 60/657,514, filed on Feb. 28, 2005.

(51) Int. Cl.
*A61K 39/395* (2006.01)

(52) U.S. Cl. .............. 424/156.1; 424/130.1; 424/134.1; 530/387.3

(58) Field of Classification Search ........................ None
See application file for complete search history.

(56) References Cited

U.S. PATENT DOCUMENTS

| | | | |
|---|---|---|---|
| 4,704,366 A | 11/1987 | Juarez-Salinas et al. | |
| 4,801,687 A | 1/1989 | Ngo | |
| 4,935,496 A | 6/1990 | Kudo | |
| 4,946,778 A | 8/1990 | Ladner | |
| 5,502,167 A | 3/1996 | Waldmann | |
| 5,530,101 A | 6/1996 | Queen et al. | |
| 5,536,814 A | 7/1996 | Ruoslahti | |
| 5,558,864 A | 9/1996 | Bendig | |
| 5,639,641 A | 6/1997 | Pedersen | |
| 5,677,181 A | 10/1997 | Parish | |
| 5,693,493 A | 12/1997 | Robinson | |
| 5,698,417 A | 12/1997 | Robinson | |
| 5,705,154 A | 1/1998 | Dalie | |
| 5,750,078 A | 5/1998 | Shitara | |
| 5,770,403 A | 6/1998 | Abrams | |
| 5,874,081 A | 2/1999 | Parish | |
| 5,922,676 A | 7/1999 | Pasqualini | |
| 6,123,941 A | 9/2000 | Bissell et al. | |
| 6,171,586 B1* | 1/2001 | Lam et al. ................ | 424/130.1 |
| 6,852,318 B1 | 2/2005 | Varner | |
| 2002/0172675 A1 | 11/2002 | Varner | |
| 2004/0077544 A1 | 4/2004 | Varner | |
| 2004/0259152 A1 | 12/2004 | Murray et al. | |
| 2005/0002930 A1* | 1/2005 | Johnson et al. ............ | 424/144.1 |
| 2005/0054834 A1 | 3/2005 | Ramakrishnan et al. | |

FOREIGN PATENT DOCUMENTS

| | | |
|---|---|---|
| EP | 0 896 002 | 2/1999 |
| WO | WO 95/14714 | 6/1995 |
| WO | WO 95/22618 | 8/1995 |
| WO | WO 97/33887 | 9/1997 |
| WO | WO 99/37329 * | 7/1999 |
| WO | WO 99/55913 | 11/1999 |
| WO | WO 99/58139 | 11/1999 |
| WO | WO 01/11086 | 2/2001 |
| WO | WO 01/53262 | 7/2001 |
| WO | WO 01/53297 | 7/2001 |
| WO | WO 01/54723 * | 8/2001 |
| WO | WO 02/079492 | 10/2002 |
| WO | WO 2004/056308 | 7/2004 |
| WO | WO 2004/110498 A | 12/2004 |
| WO | PCT/US2004/010422 | 2/2005 |

OTHER PUBLICATIONS

Duro, et al., International Journal of Pharmaceutics, May 14, 1998, pp. 211-216.*
: Mahler et al., European Journal of Pharmaceutics, vol. 59, pp. 407-417, Jan. 19, 2005.*
Conforti, et al., "Human endothelial cells express integrin receptors on the luminal aspect of their membrane," *Blood*, 80(2):437-446 (1992).
Varner, et. al, "Antagonist of Vascular Cell Integrin Alpha5beta1 Inhibit Angiogenesis" *Circulation, American Heart Association*, 98(17):abstract (1998).
Wu, H., et. al., "The Expression Of Integrin Alph5beta1 And Transforming Growth Factor-Beta In Pulmonary Fibrosis Of Rat" *Chinese Journal of Pathology*, 28(6): abstract (1999).
Zhao, Ming Wei et. al., A Distinct Integrin-Mediated Phagocytic Pathway For Extracellular Matrix Remodeling By RPE Cells: *Invest. Ophthalmol. Vis. Sci.*, 40(11):2713-2723 (1999).
Wilson, Sylvia et. al.,. "Fibronectin Fragments Promote Human Retinal Endothelial Cell Adhesion and Proliferation and ERK Activation Through Alph5beta1 Integrin and PI 3-Kinase" *Invest. Ophthalmol. Vis. Sci.*, 44(4):1704-1715 (2003).

(Continued)

*Primary Examiner*—Misook Yu
(74) *Attorney, Agent, or Firm*—Sughrue Mion PLLC

(57) ABSTRACT

The present invention provides methods for direct killing of cancer cells using anti-α5β1 antibodies. Generally, the method comprises contacting a cancer cell that expresses α5β1 on its surface with an anti-α5β1 antibody, and thereby inducing the death of the cancer cell. The methods of the invention may be employed at an early stage of cancer development in a patient to prevent tumor establishment. In addition, the methods may be used to treat previously formed tumors especially in cancer that have not proven susceptible to anti-angiogenesis therapy. The methods may be employed as a combination therapy of anti-α5β1 antibodies together with cancer chemotherapeutic agents or other molecular-based cancer therapeutic agents.

13 Claims, 2 Drawing Sheets

OTHER PUBLICATIONS

Loike, J.D. et. al., "Blockade Of Alpa 5 Beta 1 Integrins Reverses The Inhibitory Effect Of Tenacin On Chemotaxis Of Human Monocytes And Polymorphonuclear Leukocytes Through Three-Dimensional Gels Of Extracellular Matrix Proteins" *Journal of Immunology* 166(12):7534-7542 2001.

Kim, Semi et. al., "Regulation Of Integrin Alpha5beta3-Mediated Endothelial Cell Migration And Angiogenesis By Integrin Alpha5beta1 And Protein Kinase A" *Journal of Biological Chemistry*, 275(43):33920-33928 (2000).

Tolentino, Michael, J., et. al., "Angiography Of Fluoresceinated Anti-Vascular Endothelial Growth Factor Antibody And Dextrans In Experimental Choroidal Neovascularization" *Archives of Ophthalmology*, 118(1):78-84 (2000).

Ryan, S.J., "The Development Of An Experimental Model Of Subretinal Neovascularization In The Disciform Macular Degeneration" *Transactions of the American Ophthalmological Society* 77:707-745, (1979).

Grossniklaus, Hans et. al., "Immunohistochemical And Histochemcial Properties Of Surgically Excised Subretinal Neovascular Membranes In Age-Related Macular Degeneration" *American Journal of Ophthalmology* 114(4):464-472 (1992).

PCT/US05/09939: International Search Report, Mar. 24, 2005.

Storgard, Chris M. et al., "Decreased Angiogenesis and Arthritic Disease in rabbits Treated with an αvβ3 Antagonist", *The Journal of clinical Investigation*, vol. 103 (1999), pp. 47-54.

Ryan, S.J., "Subretinal Neovascularization: Natural History of an Experimental Model", *Archives of Ophthalmology*, vol. 100 (1982), pp. 1804-1809.

Rudikoff et al., P.N.A.S. USA, vol. 79 (1982), pp. 1979-83.

Pytela et al., Cell, vol. 40 (1985), pp. 191-198.

Thorpe et al., "Monoclonal Antibodies in Biological Clinical Applications", (1985), pp. 475-506.

Argraves et al., *J. Biol. Chem.*, vol. 261(28) (1986), pp. 12922-12924.

Amit, et. al., *Science*, vol. 233 (1986), pp. 747-753.

Hackett, R., et al., (1996) Dermatotoxicology. $5^{th}$ Edition. (Ed. By F.B. Marzulli and H.I. Maibach) Hemisphere Publishing Corp., Washington, D.C.

Varner et. al., "Inteqrins and Cancer", *Current Opinion in Cell Biology*, vol. 8(5) (1996), pp. 724-730.

Varner et al., "Tumor Angiogenesis and the Role of Vascular Cell Integrin Alphavbeta3," *Important Advances in Oncology*. (1996), pp. 69-87.

Van Der Loo Johannes C.M. et.al., "VLA-5 is Expressed by Mouse and Human Long-Term Repopulating Hematopoietic Cells and Mediates Adhesion to Extracellular Matrix Protein Fibronectin", *Journal of Clinical Investigation*, vol. 102 (5) (1998), pp. 1051-1061.

Wu, et. al., *J. Mol. Biol.*, vol. 294 (1999), pp. 151-162.

Edelman and Castro, "Quantitative Image Analysis of Laser-Induced Choroidal Neovascularization in Rat." *Exp. Eve Res.* vol. 71 (2000). pp. 523-533.

Kim, S. et.al., "Regulation of Angiogenesis in Vivo by Ligation of Integrin Alpha5beta1 with the Central Cell-Binding Domain of Fibronectin", *American Journal of Pathology*, vol. 156 (4) (2000), pp. 2000-2004.

Wong, et. al., *Current Eye Research*, vol. 22(2) (2001), pp. 140-147.

Sequence search alignment for SEQ ID NOS: 1 and 7 (pp. 1-2).

Zhao, et. al., *J. Cell Biol.*, vol. 152 (9) (2001), pp. 65-71.

Josic, D. et.al., "Analytical and Preparative Methods for Purification of Antibodies", *Food Technology and Biotechnology*, vol. 39 (3) (2001), pp. 215-226.

03796541.5, Supplementary European search report, Aug. 24, 2007.

Vajdos, et. al., *J. Molec. Biol.*, vol. 320 (2002), pp. 415-428.

"Eos Biotechnology Files Investigational New Drug for Novel Targets with Anti-Angiogenic Properties", www.pharmabiz.com/article/detnews.asp?articleid=13491&sectionid=14&z=y>, (2002).

"Protein Design Labs to Acquire Eos Biotechnology", www.pharmabiz.com/article/detnews.asp?articleid=14199&sectionid=14&z=y>, (2003).

Proulx et al., "Effect of Quiescence on Integrin ÿÿ Expression in Human Retinal Pigment Epithelium", *Molecular Vision*. vol. 9 (2003) pp. 473-481.

Ramakrishnan Vanitha et.al., "A Function-Blocking Chimeric Antibody Eos200-4, Against Alpha5beta1 Integrin Inhibits Angiogenesis in a Monkey Model", *Proceedings of the American Association for Cancer Research Annual Meeting*, vol. 44 (2003), pp. 605-606.

Ho Sun K. et al., "The Effect of a Chimeric Anti-Integrin Alpha5beta1 Antibody (M200) on the Migration of HUVECs and Human Cancer Cells", *Proceedings of the American Association for Cancer Research Annual Meeting*, vol. 45 (2004), p. 333.

Bhaskar Vinay et al., "M200 (volociximab), a Chimeric Antibody against Integrin Alpha5beta1, Inhibits Tumor Growth by Multiple mechanisms", *Proceedings of the American Association for Cancer Research Annual Meeting, vol. 46 (2005), pp. 1063 & $96^{th}$ Annual Meeting of the American Association for Cancer Research*, (2005).

PCT/US2003/038172—International Search Report dated Jul. 8, 2005.

Ramakrishnan Vanitha et.al., "Preclinical Evaluation of an Anti-[Alpha]5[beta]1 Integrin Antibody as a Novel Anti-Angiogeneic Agent", *Journal of Experimental Therapeutics and Oncology*, vol. 5 (4) (2006), pp. 273-286.

Valera Pharmaceuticals, Press Release: *Hydron Implant Technology*, pp. 1.

Valera Pharmaceuticals, Technology Release: *Hydron Implant Technology*, pp. 1.

Kuwada S.K., "Volociximab, an Angiogenesis Inhibiting Chimeric Monoclonal Antibody", *Current Opinion In Molecular Therapeutics*), vol. 9 (1) (2007), pp. 92-98.

U.S. Food and Drug Administration: "Rituxan," Internet Article [Online] 2002, Retrieved from the Internet: URL: http://www.acessdata.fda.gov/scripts/cder/onctools/labels.cfm?GN=Rituximab> [retrieved on Jun. 17, 2008 ].

Wang Wei: "Instability, stabilization, and formulation of liquid protein pharmaceuticals," International Journal of Pharmaceutics, Amsterdam, vol. 185, No. 2, Aug. 20, 1999, pp. 129-188.

Stoeltzing Oliver et al:"Inhibition of integrin alpha5beta1 function with a small peptide (ATN-161) plus continuous 5-FU infusion reduces colorectal liver metastases and improves survival in mice," Internation Journal of Cancer, New York, NY, vol. 104, No. 4, Apr. 20, 2003, pp. 496-503.

Murillo C A et al: "Inhibition of alpha5beta1 integrin decreases PI3K activation and cell adhesion of human colon cancers," Surgery, C.V. Mosby CO., St. Louis, vol. 136, No. 2, Aug. 1, 2004, pp. 143-149.

Daugherty et al: "Formulation and delivery issues for monoclonal antibody therapeutics," Advanced Drug Delivery Reviews, Amsterdam, NL, vol. 58, No. 5-6, Aug. 7, 2006, pp. 686-706.

Supplementary European Search Report of EP 05 74 4016.

\* cited by examiner

A. IIA1 V_H sequences
[NA, SEQ ID NO: 1; AA, SEQ ID NO: 2]

```
  1  ATGGCTGTCCTGGGGCTGCTTCTCTGCCTGGTGACTTTCCCAAGCTGTGTCCTGTCCCAG
     M   A   V   L   G   L   L   L   C   L   V   T   F   P   S   C   V   L   S   Q
 61  GTGCAGCTGAAGGAGTCAGGACCTGGCCTGGTGGCGCCCTCACAGAGCCTGTCCATCACA
     V   Q   L   K   E   S   G   P   G   L   V   A   P   S   Q   S   L   S   I   T
121  TGCACCATCTCAGGGTTCTCATTAACCGACTATGGTGTTCACTGGGTTCGCCAGCCTCCA
     C   T   I   S   G   F   S   L   T   D   Y   G   V   H   W   V   R   Q   P   P
181  GGAAAGGGTCTGGAGTGGCTGGTAGTGATTTGGAGTGATGGAAGCTCAACCTATAATTCA
     G   K   G   L   E   W   L   V   V   I   W   S   D   G   S   T   Y   N   S
241  GCTCTCAAATCCAGAATGACCATCAGGAAGGACAACTCCAAGAGCCAAGTTTTCTTAATA
     A   L   K   S   R   M   T   I   R   K   D   N   S   K   S   Q   V   F   L   I
301  ATGAACAGTCTCCAAACTGATGACTCAGCCATGTACTACTGTGCCAGACATGGAACTTAC
     M   N   S   L   Q   T   D   D   S   A   M   Y   Y   C   A   R   H   G   T   Y
361  TACGGTATGACTACGACGGGGGATGCTTTGGACTACTGGGGTCAAGGAACCTCAGTCACC
     Y   G   M   T   T   T   G   D   A   L   D   Y   W   G   Q   G   T   S   V   T
421  GTCTCCTCA
     V   S   S
```

B. IIA1 V_L sequences
[NA, SEQ ID NO: 3; AA, SEQ ID NO: 4]

```
  1  ATGGATTTTCAGGTGCAGATTTTCAGCTTCCTGCTAATCAGTGCCTCAGTCATAATGTCC
     M   D   F   Q   V   Q   I   F   S   F   L   L   I   S   A   S   V   I   M   S
 61  AGAGGACAAATTGTTCTCACCCAGTCTCCAGCAATCATGTCTGCATCTCTAGGGGAACGG
     R   G   Q   I   V   L   T   Q   S   P   A   I   M   S   A   S   L   G   E   R
121  GTCACCATGACCTGCACTGCCAGTTCAAGTGTAAGTTCCAATTACTTGCACTGGTACCAG
     V   T   M   T   C   T   A   S   S   S   V   S   S   N   Y   L   H   W   Y   Q
181  CAGAAGCCAGGATCCGCCCCCAATCTCTGGATTTATAGCACATCCAACCTGGCTTCTGGA
     Q   K   P   G   S   A   P   N   L   W   I   Y   S   T   S   N   L   A   S   G
241  GTCCCAGCTCGTTTCAGTGGCAGTGGGTCTGGGACCTCTTACTCTCTCACAATCAGCAGC
     V   P   A   R   F   S   G   S   G   S   G   T   S   Y   S   L   T   I   S   S
301  ATGGAGGCTGAAGATGCTGCCACTTATTACTGCCACCAGTATCTTCGTTCCCCACCGACG
     M   E   A   E   D   A   A   T   Y   Y   C   H   Q   Y   L   R   S   P   P   T
361  TTCGGTGGAGGCACCAAGCTGGAAATCAAA
     F   G   G   G   T   K   L   E   I   K
```

FIGURE 1

A. M200 V$_H$ sequences
[NA, SEQ ID NO: 5; AA, SEQ ID NO: 6]

```
  1    TCTAGACCACCATGGCTGTCCTGGGGCTGCTTCTCTGCCTGGTGACTTTCCCAAGCTGTG
                      M  A  V  L  G  L  L  L  C  L  V  T  F  P  S  C
 61    TCCTGTCCCAGGTGCAGCTGAAGGAGTCAGGACCTGGCCTGGTGGCGCCCTCACAGAGCC
        V  L  S  Q  V  Q  L  K  E  S  G  P  G  L  V  A  P  S  Q  S
121    TGTCCATCACATGCACCATCTCAGGGTTCTCATTAACCGACTATGGTGTTCACTGGGTTC
        L  S  I  T  C  T  I  S  G  F  S  L  T  D  Y  G  V  H  W  V
181    GCCAGCCTCCAGGAAAGGGTCTGGAGTGGCTGGTAGTGATTTGGAGTGATGGAAGCTCAA
        R  Q  P  P  G  K  G  L  E  W  L  V  V  I  W  S  D  G  S  S
241    CCTATAATTCAGCTCTCAAATCCAGAATGACCATCAGGAAGGACAACTCCAAGAGCCAAG
        T  Y  N  S  A  L  K  S  R  M  T  I  R  K  D  N  S  K  S  Q
301    TTTTCTTAATAATGAACAGTCTCCAAACTGATGACTCAGCCATGTACTACTGTGCCAGAC
        V  F  L  I  M  N  S  L  Q  T  D  D  S  A  M  Y  Y  C  A  R
361    ATGGAACTTACTACGGAATGACTACGACGGGGGATGCTTTGGACTACTGGGGTCAAGGAA
        H  G  T  Y  Y  G  M  T  T  G  D  A  L  D  Y  W  G  Q  G
421    CCTCAGTCACCGTCTCCTCAG^GTAAGAATGGCCTCTAGA
        T  S  V  T  V  S  S
```

B. M200 V$_L$ sequences
[NA, SEQ ID NO: 7; AA, SEQ ID NO: 8]

```
  1    ACGCGTCCACCATGGATTTTCAGGTGCAGATTTTCAGCTTCCTGCTAATCAGTGCCTCAG
                     M  D  F  Q  V  Q  I  F  S  F  L  L  I  S  A  S
 61    TCATAATGTCCAGAGGACAAATTGTTCTCACCCAGTCTCCAGCAATCATGTCTGCATCTC
        V  I  M  S  R  G  Q  I  V  L  T  Q  S  P  A  I  M  S  A  S
121    TAGGGGAACGGGTCACCATGACCTGCACTGCCAGTTCAAGTGTCAGTTCCAATTACTTGC
        L  G  E  R  V  T  M  T  C  T  A  S  S  S  V  S  S  N  Y  L
181    ACTGGTACCAGCAGAAGCCAGGATCCGCCCCCAATCTCTGGATTTATAGCACATCCAACC
        H  W  Y  Q  Q  K  P  G  S  A  P  N  L  W  I  Y  S  T  S  N
241    TGGCTTCTGGAGTCCCAGCTCGTTTCAGTGGCAGTGGGTCTGGGACCTCTTACTCTCTCA
        L  A  S  G  V  P  A  R  F  S  G  S  G  S  G  T  S  Y  S  L
301    CAATCAGCAGCATGGAGGCTGAAGATGCTGCCACTTATTACTGCCACCAGTATCTTCGTT
        T  I  S  S  M  E  A  E  D  A  A  T  Y  Y  C  H  Q  Y  L  R
361    CCCCACCGACGTTCGGTGGAGGCACCAAGCTGGAAATCAAAC^GTAAGTAGAATCCAAAGT
        S  P  P  T  F  G  G  G  T  K  L  E  I  K
421    CTAGA
```

FIGURE 2

USE OF ANTI-α5β1 ANTIBODIES TO INHIBIT CANCER CELL PROLIFERATION

CROSS REFERENCE TO RELATED APPLICATIONS

This application claims priority from U.S. Provisional Application Nos. 60/556,421, filed Mar. 24, 2004, 60/556,422, filed Mar. 24, 2004, 60/625,049, filed Nov. 3, 2004, 60/651,098, filed Feb. 7, 2005, and 60/657,514, filed Feb. 28, 2005, each of which is hereby incorporated by reference in its entirety.

FIELD OF THE INVENTION

The present invention provides antibodies that specifically recognize α5β1 integrin expressed on the surface of cancer cells, and methods for using the antibodies to inhibit proliferation of these cancer cells.

BACKGROUND OF THE INVENTION

The association of α5β1 integrin with tumor angiogenesis is well-established (see, e.g., U.S. Publ. Pat. Appl. U.S. 2002/0172675 A1, filed May 7, 1999, which is hereby incorporated by reference herein). α5β1 is a heterodimeric integrin that specifically binds the ligand fibronectin. α5β1 is expressed on the surface of endothelial cells and mediates adhesion to and migration toward fibronectin. The binding interaction between α5β1 and fibronectin has been shown to be important for tumor angiogenesis. Angiogenesis within a tumor begins when the release of one or more pro-angiogenic growth factors (e.g., FGF, VEGF, PDGF, etc.) locally activates the endothelial cells. These activated endothelial cells then form new blood vessels by binding, via their α5β1 integrin, to the fibronectin in the extracellular matrix. Anti-α5β1 antibodies have been shown to inhibit angiogenesis in in vivo tumor models (see, e.g., U.S. 2002/0172675 A1).

Anti-angiogenesis cancer therapy is based on inhibiting tumor vascularization and thereby preventing continued tumor growth and metastasis (for reviews see, e.g., Marx, "A Boost for Tumor Starvation," *Science* 301, 452 (2003); Sato, "Molecular Diagnosis of Tumor Angiogenesis and Anti-Angiogenic Cancer Therapy," *Int. J. Clin. Oncol.* 8, 200 (2003); Bissachi et al., "Anti-Angiogenesis and Angioprevention: Mechanisms, Problems and Perspectives," *Cancer Detec. Prev.* 27, 229 (2003)). More than 60 anti-angiogenesis based therapeutics currently are in clinical development for cancer treatment. While in some cancers, it may be possible to "starve" a tumor by preventing its vascularization, current research shows that there are cancers that do not appear to be vulnerable to anti-angiogenesis treatment (see, Sato, supra). For example, the anti-VEGF antibody therapeutic, AVASTIN™ (bevacizumab) succeeded in clinical trials for colon cancer but not breast cancer (see, Marx, supra). In addition, anti-angiogenesis based therapeutic methods are not well-suited to early-stage treatment when the tumor vascularization process has not yet begun.

Due to its function in angiogenesis, the α5β1 integrin has been proposed as a therapeutic target for numerous diseases mediated by angiogenic processes including cancerous tumor growth. Chimeric and humanized antibodies to α5β1 have been developed that block specific binding to fibronectin. A chimeric α5β1 antibody, M200 (also known by its generic name, volociximab) has been shown to induce apoptosis of activated endothelial cells in vitro regardless of the growth factor stimulus.

Thus, there remains a need for cancer therapies and early-stage treatment methods capable of directly killing cancer cells before the tumor vascularization process even begins, or for when a targeted anti-angiogenesis therapy proves ineffective.

SUMMARY OF THE INVENTION

The present invention provides methods of killing cancer cells using anti-α5β1 antibodies. In a general embodiment, the method comprises contacting a cancer cell that expresses α5β1 on its surface with an anti-α5β1 antibody.

In one preferred embodiment, the invention provides a method of inhibiting proliferation of a cancer (or tumor) cell that expresses α5β1 integrin on its surface comprising contacting the tumor cell with an antibody that binds to the α5β1 integrin expressed on the tumor cell surface. In a preferred embodiment, the tumor cell is in a patient with a refractory solid tumor. In another preferred embodiment, the tumor cell is from a cancer selected from the group consisting of: bladder cancer, breast cancer, colon cancer, fibrosarcoma, lung cancer, metastatic melanoma, pancreatic cancer, prostate cancer, ovarian cancer, renal cell carcinoma and spleen cancer.

In another embodiment, the invention provides a method of inducing death of a tumor cell that expresses α5β1 integrin on its surface comprising contacting the tumor cell with an antibody that binds to the α5β1 integrin expressed on the tumor cell surface. In a preferred embodiment, the tumor cell is in a patient with a refractory solid tumor. In another preferred embodiment, the tumor cell is from a cancer selected from the group consisting of bladder cancer, breast cancer, colon cancer, fibrosarcoma, lung cancer, metastatic melanoma, pancreatic cancer, prostate cancer, ovarian cancer, renal cell carcinoma and spleen cancer.

In a further embodiment, the invention provides a method of inhibiting the proliferation of a cancer cell in a patient wherein the cancer cell expresses α5β1 integrin on its surface. In this embodiment, the method comprises administering to the patient a therapeutically effective amount of an antibody, wherein the antibody competitively inhibits binding of M200 to α5β1 integrin on the cancer cell surface. In another embodiment, the antibody comprises a variable region with an amino acid sequence substantially identical to SEQ ID NOs: 2, 4, 6 and 8. In a preferred embodiment of this method, the antibody administered to the patient neutralizes at least one biological activity of α5β1 integrin. In another embodiment, the antibody administered to the patient comprises a therapeutic effector moiety (e.g., an antibody-drug conjugate). In still a further embodiment of this method, the antibody is administered to the patient, serially, or together with, another chemotherapeutic agent. In another preferred embodiment of this method, the antibody is administered to a patient with a refractory solid tumor, serially, or together with, another chemotherapeutic agent.

In another embodiment, the invention provides a method for treating a subject suspected of developing a cancer that expresses α5β1 on its cell surface wherein the subject has not yet developed a tumor comprising, administering to the patient a therapeutically effective amount of a pharmaceutical composition comprising an antibody binds to the α5β1 integrin. In a preferred embodiment, the cancer is selected from the group consisting of bladder cancer, breast cancer, colon cancer, fibrosarcoma, lung cancer, metastatic melanoma, pancreatic cancer, prostate cancer, ovarian cancer, renal cell carcinoma and spleen cancer.

In another embodiment, the invention provides a method of treating a subject with a genetic predisposition for a cancer that expresses α5β1 wherein the subject has not yet developed a tumor comprising administering to the subject a therapeutically effective amount of a pharmaceutical composition comprising an antibody binds to the α5β1 integrin. In a preferred embodiment, the cancer is selected from the group consisting of bladder cancer, breast cancer, colon cancer, fibrosarcoma, lung cancer, metastatic melanoma, pancreatic cancer, prostate cancer, ovarian cancer, renal cell carcinoma and spleen cancer.

The preferred anti-α5β1 antibodies useful with the methods of the invention include IIA1, M200, F200, and antibodies that specifically bind to the same epitope on α5β1 as IIA1, M200, and F200.

In another embodiment, the anti-α5β1 antibodies useful with the methods of the invention include antibodies that competitively inhibit binding of IIA1 and/or M200 to α5β1 integrin expressed on the tumor cell surface.

Other antibodies useful with the method of the invention include antibodies comprising a variable region amino acid sequence substantially identical to SEQ ID NOs: 2, 4, 6 and 8. Also, included are antibodies comprising variable region amino acid sequences with at least about 90%, 95%, 98% or preferably, 99% or greater identity to SEQ ID NOs: 2, 4, 6 and 8.

In another embodiment, the present invention provides anti-α5β1 antibodies formulated as pharmaceutical compositions. These pharmaceutical compositions are useful in the various methods of the invention disclosed herein. In various embodiments, the anti-α5β1 antibody pharmaceutical compositions may be administered in a therapeutically effective amount to a subject by various routes including, but not limited to, orally, subcutaneously, topically, intravenously, intranasally, transdermally, intraperitoneally, intramuscularly, intrapulmonary, vaginally, rectally, intraocularly, intraventricularly, or intrathecally. In a preferred embodiment, the pharmaceutical composition is a liquid formulation comprising between about 1.0 mg/mL and 15 mg/mL of an anti-α5β1 antibody, about 22-27 mM citrate, about 145-165 mM sodium chloride, about 0.04% to 0.06% polysorbate (TWEEN®) 80, at a pH of about 5.5 to 7.5. In another preferred embodiment, the pharmaceutical composition is a liquid formulation comprising about 10 mg/mL anti-α5β1 antibody, about 25 mM citrate, about 150 mM sodium chloride, about 0.05% polysorbate (TWEEN®) 80, at a pH of about 6.5. In a particularly preferred embodiment, the pharmaceutical composition is a liquid formulation comprising about 10 mg/mL M200, about 25 mM citrate, about 150 mM sodium chloride, about 0.05% polysorbate (TWEEN®) 80, with a pH of about 6.5. In other preferred embodiments, each of the pharmaceutical compositions described herein may further comprise a chemotherapeutic agent. In another embodiment, the pharmaceutical composition comprising an anti-α5β1 antibody may be administered to a patient together with a pharmaceutically effective amount of another chemotherapeutic agent.

The pharmaceutical compositions described above may be used in a method of treating a patient diagnosed with or suspected of having a cancer selected from the group consisting of: bladder cancer, breast cancer, colon cancer, fibrosarcoma, lung cancer, metastatic melanoma, pancreatic cancer, prostate cancer, ovarian cancer, renal cell carcinoma and spleen cancer, with the method comprising: administering intravenously to the patient a therapeutically effective dose of the liquid formulation comprising between about 1.0 mg/mL and 15 mg/mL of an anti-α5β1 antibody, about 22-27 mM citrate, about 145-165 mM sodium chloride, about 0.04% to 0.06% polysorbate (TWEEN®) 80, at a pH of about 5.5 to 7.5. In one embodiment of the treatment methods, the therapeutically effective dose administered is about 10 mg/kg. In a preferred embodiment, the patient treated with the pharmaceutical composition has been diagnosed with or is suspected of having renal cell carcinoma or metastatic melanoma, and the therapeutically effective dose is about 10 mg/kg.

BRIEF DESCRIPTION OF THE DRAWINGS

FIG. 1 depicts: (A) IIA1 $V_H$ nucleic acid sequence (SEQ ID NO: 1) and amino acid sequence (SEQ ID NO: 2); (B) IIA1 $V_L$ nucleic acid sequence (SEQ ID NO: 3) and amino acid sequence (SEQ ID NO: 4).

FIG. 2 depicts: (A) M200 $V_H$ nucleic acid sequence (SEQ ID NO: 5) and amino acid sequence (SEQ ID NO: 6); (B) M200 $V_L$ nucleic acid sequence (SEQ ID NO: 7) and amino acid sequence (SEQ ID NO: 8).

DETAILED DESCRIPTION OF THE INVENTION

For clarity and understanding, the following disclosure describes the invention in detail by way of illustrative embodiments and exemplifications. The embodiments and examples included in this disclosure are not intended to limit the scope of the invention. It will be readily apparent to one of ordinary skill in the art that equivalent materials and/or methods may be employed, and/or obvious changes, variations or modifications may be made in any of the disclosed embodiments and examples without departing from the scope of the appended claims.

All publications and patent applications cited in this disclosure are herein incorporated by reference as if each individual publication or patent application were specifically and individually indicated to be incorporated by reference.

Unless defined otherwise, all terms used herein have the common ordinary meaning ascribed to them by a person of ordinary skill in the art to which this invention belongs.

Overview

The present invention is based on the surprising discovery that α5β1 integrin is expressed on the surface of tumor epithelial cells for many types of cancer. Further, it has been found that targeted antibody binding to this surface α5β1 results in direct killing of these cancer cells. Because this method of attacking and killing cancer cells is direct, it is amenable to very early-stage treatment (i.e., prior to substantial tumor formation). Furthermore, the direct cancer cell killing method of the present invention may be particularly useful for treating cancers that express α5β1 on the cell surface but have not proven susceptible to anti-angiogenic approaches. Cancers in this category include, but are not limited to, bladder cancer, breast cancer, renal cancer, pancreatic cancer, lung cancer, prostate cancer, ovarian cancer, and metastatic melanoma.

The present invention provides methods of killing or otherwise preventing the proliferation of cancer cells using anti-α5β1 antibodies. In its most general embodiment, the method comprises contacting a cancer cell that expresses α5β1 on its surface with an anti-α5β1 antibody, and thereby inducing the death (e.g., via apoptosis) of the cancer cell.

The methods of the invention may be employed to kill cancer cells in vivo (e.g., in a patient) and thereby prevent or attenuate tumor formation and growth. In addition, the method may be used to treat previously formed tumors, and may be employed together with other cancer therapies (e.g., chemotherapeutic agents or other molecular-based cancer therapeutic agents). For example, a patient suffering from the growth of a cancerous tumor may be treated with a formulation of the antibody M200 in tandem with a chemotherapeutic compound such as doxorubicin. Because M200 is a chimeric antibody with relatively low toxicity in humans, this combination treatment may provide comparable cancer cell killing power without the toxic side effects associated with a higher dosage of the chemotherapeutic alone.

The present invention provides a method in which anti-α5β1 antibodies kill and/or inhibit the proliferation of cancer cells directly, even in the absence of any tumor vasculature that may be susceptible to the anti-angiogenic effect of these antibodies. Therefore, the method is particularly well-suited for the prophylaxis or therapeutic treatment of cancers that express α5β1 but do not form heavily vascularized tumors, and/or are not otherwise susceptible to anti-angiogenesis therapeutics e.g., pancreatic cancer, renal cancer, metastatic melanoma, lung cancer and breast cancer.

Furthermore, because of the direct cancer cell killing ability of M200 (and other anti-α5β1 antibodies disclosed herein) it is possible to use these antibodies in early stage cancer therapy prior to the formation of vascularized tumors. An early-stage treatment method is particularly significant in view of the advent of new, more sensitive diagnostic tests for cancers that have been developed with the genetic marker information mined from the human genome sequence. It is likely that many common cancers will be detected and diagnosed at a very early stage, i.e., a pretumor stage wherein cancer cells may be present in tissue and/or circulating but have not established a tumor structure detectable by less sensitive non-genetic diagnostics. In such an early stage diagnosis scenario, anti-angiogenesis therapies may have little or no effect when a tumor vasculature has not yet been established and common chemotherapeutics may create too many toxic side-effects to warrant their use. Because the method of the present invention results in antibody-targeted direct killing of cancer cells that express α5β1 integrin on their surface it is particularly well-suited for early-stage preventative treatment.

Those subjects most likely to benefit from the early-stage method of treatment would include, but are not limited to: 1) a subject who has had pretumor tests indicating a high probability of the development and/or presence of tumors (or microtumors); 2) a subject exposed to a very potent carcinogenic environment whose probability of tumor progression is high; and, 3) a subject whose has a high genetic predisposition to develop a cancer wherein the cancer cells express α5β1 on their surface.

Anti-α5β1 Antibodies

The methods of the present invention employ anti-α5β1 antibodies as direct cancer cell killing agents. As used herein, the term "antibody" refers to an immunoglobulin molecule that specifically binds to, or is immunologically reactive with a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including e.g., Fab', F(ab')$_2$, Fab, Fv, rIgG, and scFv fragments. The term "scFv" refers to a single chain Fv antibody in which the variable domains of the heavy chain and the light chain from a traditional antibody have been joined to form one chain. In addition, the term "antibody," as used in the context of the invention disclosed herein encompasses mixtures of more than one antibody reactive with a specific antigen (e.g., a cocktail of different types of monoclonal antibodies reactive with α5β1 integrin).

Preferably, the anti-α5β1 antibodies used in the methods of the present invention are monoclonal antibodies. Monoclonal antibodies useful with the methods present invention may be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, New York (1981), pp. 563-681 (both of which are incorporated herein by reference in their entireties). Production of antibodies by selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

In preferred embodiments, the direct cancer cell killing methods of the present invention may be carried out using the previously characterized anti-α5β1 antibodies, IIA1, M200, or F200. IIA1 is the parent mouse IgG1 class antibody that has been shown to inhibit α5β1 integrin binding to fibronectin (see, e.g., U.S. Publ. Pat. Appl. U.S. 2002/0172675 A1, filed May 7, 1999, which is hereby incorporated by reference herein). M200 is a chimeric IgG4 antibody derived from IIA1. F200 is a Fab fragment derived from M200. These antibodies have been generated, functionally characterized and their specific amino acid sequences disclosed in U.S. patent application Ser. Nos. 10/724,274, filed Nov. 26, 2003, and Ser. No. 10/830,956, filed Apr. 23, 2004, each of which is hereby incorporated by reference herein. Both M200 and F200 have been shown to exhibit in vivo anti-angiogenic efficacy in monkey eye and rabbit eye models (see, U.S. patent application Ser. Nos. 10/724,274, filed Nov. 26, 2003, and Ser. No. 10/830,956, filed Apr. 23, 2004).

Antibodies useful with the method of the present invention also include those that specifically bind to the same epitope on α5β1 as IIA1, M200, and F200. An "epitope" (or "antigenic determinant") refers to a site on an antigen to which an antibody binds. Epitopes may be formed both from contiguous amino acids or noncontiguous amino acids juxtaposed by tertiary folding of a protein. For example, the epitope on α5β1 integrin may comprise amino acids on each of the α and β polypeptide chains that make up the heterodimer structure. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 6-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

Two antibodies are said to bind to the same epitope of a protein if amino acid mutations in the protein that reduce or eliminate binding of one antibody also reduce or eliminate binding of the other antibody. Also, it may be concluded that two antibodies bind the same epitope if the two antibodies compete for binding to the protein, i.e., binding of one antibody to the protein competitively inhibits, reduces or eliminates binding of the other antibody. Consequently, the methods of the present invention may be carried out with an antibody that has been determined to competitively inhibit the binding of IIA1, M200 (volociximab), or F200 to α5β1 integrin expressed on the cancer cell surface.

The anti-α5β1 antibodies useful with the methods of the present invention are not limited to IIA1, M200 and F200, but may include antibodies comprising a variable region, framework region, or CDR amino acid sequence substantially identical to those of IIA1, M200 and F200. The extent of the variable regions, framework regions and CDRs are well-known to those of ordinary skill in the art (see e.g., Kabat, et al., "Sequences of Proteins of Immunological Interest", 5$^{th}$ ed., National Institutes of Health, Bethesda, Md. (1991)). As used herein, the variable region of the heavy chain ("$V_H$" or "VH") or light chain ("$V_L$" or a "VL") of an antibody, includes the heavy or light chains of an antigen binding fragment, e.g., Fv, scFv, dsFv or Fab. Antibody light and heavy chain variable regions also contain four "framework" regions interrupted by three hypervariable regions, also called "complementarity-determining regions" or "CDRs." The CDRs are primarily responsible for binding to an epitope of an antigen.

A "substantially identical" variable, constant, framework region, or CDR refers to an antibody region wherein at least about 85-90%, and preferably at least 95% of the amino acid sequence is identical to a natural or unaltered antibody variable or constant region. The terms "identical" or percent "identity," in the context of two or more amino acid or nucleotide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., description of BLAST at the National Center for Biotechnology Information (NCBI) web site located at www.ncbi.nlm.nih.gov).

Identical or substantially identical sequences include sequences having deletions and/or additions, as well as those that have substitutions, as well as naturally occurring, e.g., polymorphic or allelic variants, and man-made variants such as conservatively modified variants. The well-known algorithms for measuring sequence identity can account for gaps and the like. Preferably, sequence identity exists over a region that is at least about 25 amino acids or nucleotides in length, or more preferably over a region that is 50-100 amino acids or nucleotides in length.

The amino acid sequences of the anti-α5β1 antibodies useful with the methods of the present invention are not confined to the sequences found in natural antibodies; antibodies can be redesigned to obtain desired characteristics using well-known recombinant DNA techniques. Such "genetically altered antibodies" include those where the amino acid sequence has been varied from that of a parent (i.e., unaltered) antibody. The possible variations range from the changing of just one or a few amino acids to the complete redesign of, for example, the variable or constant region. Changes, by site-directed mutation, in the constant region may be made in order to improve or alter the functional characteristics of a therapeutic antibody such as immunogenicity, pharmacokinetic characteristics (e.g., serum half-life), complement fixation, interaction with membranes and other effector functions. Generally, changes to the antibody variable region may be made in order to improve the antigen binding characteristics.

In one preferred embodiment, the chimeric antibody, M200, may be employed in the direct cancer cell killing methods of the present invention. The term "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are well-known to those of ordinary skill in the art. See e.g., Morrison et al., Science 229:1202-1207 (1985); Oi et al., BioTechniques 4:214-221 (1986); Gillies et al., J. Immunol. Methods 125:191-202 (1989); and U.S. Pat. Nos. 5,807,715; 4,816,567; and 4,816,397, each of which is hereby incorporated herein by reference in its entirety.

In another preferred embodiment, humanized anti-α5β1 antibodies may be employed in the direct cancer cell killing methods of the present invention. The additional human sequences in humanized antibodies further decrease the possible immunogenicity of the antibody when it is used as a human therapeutic. Humanized versions of IIA1 are disclosed in U.S. patent application Ser. Nos. 10/724,274, filed Nov. 26, 2003, and Ser. No. 10/830,956, filed Apr. 23, 2004, each of which is hereby incorporated by reference herein. The term "humanized antibody" refers to an immunoglobulin comprising a human framework, at least one and preferably all CDRs from a non-human antibody, and in which any constant region present is substantially identical to a human immunoglobulin constant region, i.e., at least about 85-90%, and preferably at least 95% identical. Hence, all parts of a humanized immunoglobulin, except the CDRs, are substantially identical to corresponding parts of one or more native human immunoglobulin sequences. Accordingly, such humanized antibodies are chimeric antibodies, wherein substantially less than an intact human variable domain has been substituted by the corresponding sequence from a non-human species. Framework residues in the human framework regions may be substituted with the corresponding residue from the CDR donor antibody to alter, preferably improve, antigen binding. These framework substitutions may be identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies may be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Mol. Immunol., 28:489-498 (1991); Studnicka et al., Prot. Eng. 7:805-814 (1994); Roguska et al., Proc. Natl. Acad. Sci. 91:969-973 (1994), and chain shuffling (U.S. Pat. No. 5,565,332), all of which are hereby incorporated by reference in their entireties.

In another embodiment, human antibodies (i.e., antibodies comprising both a human variable and constant region) to α5β1 may be employed for therapeutic treatment of human patients according to the methods of the present invention.

Human antibodies can be made or obtained by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. Completely human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope (Jespers et al., Biotechnology 12:899-903 (1988).

In an alternative embodiment, primatized antibodies (i.e., an antibody comprising monkey variable regions and human constant regions) may be employed for therapeutic treatment according to the methods of the present invention. Methods for producing primatized antibodies are known in the art. See e.g., U.S. Pat. Nos. 5,658,570; 5,681,722; and 5,693,780, which are incorporated herein by reference in their entireties.

Antibody Function

The methods of the present invention employ functional antibodies that exhibit specific binding to α5β1 integrin. Avidity testing of antibodies for specific binding to antigen allows one skilled in the art to identify antibodies specifically recognizing one or more epitopes of α5β1 integrin. Antibodies are defined to be specifically binding if: 1) they exhibit a threshold level of binding activity; and/or 2) they do not significantly cross-react with related polypeptide molecules.

First, anti-α5β1 antibodies useful for the methods disclosed herein specifically bind (or "specifically react" or "specifically immunoreact") if they bind to a α5β1 integrin polypeptide, peptide or epitope with a binding affinity ($K_a$) of $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (Scatchard, Ann. NY Acad. Sci. 51: 660-72, 1949), or by surface plasmon resonance using BIAcore. A variety of antibody binding assays useful for characterizing anti-α5β1 antibodies are disclosed in U.S. patent application Ser. Nos. 10/724,274, filed Nov. 26, 2003, and Ser. No. 10/830,956, filed Apr. 23, 2004, each of which is hereby incorporated by reference herein.

Second, antibodies specifically bind if they do not significantly cross-react with related polypeptides. Antibodies do not significantly cross-react with related polypeptide molecules, for example, if they detect α5β1 integrin polypeptide but not known related polypeptides using a standard Western blot analysis (see, e.g., "Current Protocols in Molecular Biology," eds. Ausubel et al., 1995). Examples of known related polypeptides include orthologs, proteins from the same species that are members of the integrin family of proteins, or mutant α5β1 integrin polypeptides where the mutation alters the anti-α5β1 epitope. Moreover, antibodies may be "screened against" known related polypeptides to isolate a population that specifically binds to the α5β1 integrin. For example, antibodies raised to human α5β1 integrin polypeptides are adsorbed to related polypeptides adhered to insoluble matrix; antibodies specific to human α5β1 integrin polypeptides will flow through the matrix under the proper buffer conditions. Such screening allows isolation of polyclonal and monoclonal antibodies non-crossreactive to closely related polypeptides (Antibodies: A Laboratory Manual, Harlow and Lane (eds.), Cold Spring Harbor Laboratory Press, 1988; Current Protocols in Immunology, Cooligan, et al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff et al., Adv. in Immunol. 43: 1-98, 1988; Monoclonal Antibodies: Principles and Practice, Goding, J. W. (eds.), Academic Press Ltd., 1996; Benjamin et al., Ann. Rev. Immunol. 2: 67-101, 1984). Representative examples of such assays include: concurrent immunoelectrophoresis, radioimmuno-assay, radioimmunoprecipitation, enzyme-linked immuno-sorbent assay (ELISA), dot blot or Western blot assay, inhibition or competition assay, and sandwich assay. For a review of immunological and immunoassay procedures, see *Basic and Clinical Immunology* (Stites & Terr eds., 7$^{th}$ ed. 1991).

Specific binding anti-α5β1 antibodies useful with the methods of the present invention may be prepared through a process of selection for α5β1 binding. Generally, polyclonal antibodies raised to specifically bind to a particular protein, or its polymorphic variants, alleles, orthologs, conservatively modified variants, splice variants, may be selected to obtain only those antibodies that are specifically immunoreactive with the selected protein (e.g., α5β1 integrin) and not with other proteins. Specific binding selection is achieved by subtracting out antibodies that cross-react with other molecules. A variety of immunoassay formats may be used to select antibodies specifically reactive with the α5β1 integrin polypeptide. For example, solid-phase ELISA immunoassays may be used to select antibodies specifically reactive with protein (see, e.g., Harlow & Lane, Antibodies, A Laboratory Manual (1988) for a description of immunoassay formats and conditions that can be used to determine specific immunoreactivity).

Antibody Drug Conjugates

In some embodiments, the method of killing cancer cells may employ an anti-α5β1 antibody conjugated to an effector moiety. The effector moiety may be any number of molecules, including labeling moieties such as radioactive labels or fluorescent labels, or preferably may be a therapeutic moiety. The effector moiety (or "effector component") may be bound (or linked, or conjugated), to the anti-5β1 antibody either covalently, through a linker or a chemical bond, or noncovalently, through ionic, van der Waals, electrostatic, or hydrogen bonds.

In one aspect the therapeutic moiety is a small molecule that modulates the activity of the α5β1 integrin. In another aspect, the therapeutic moiety affects the activity of molecules or cells associated with or in close proximity to the α5β1 integrin. For example, the therapeutic moiety may be a cytotoxic agent. The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof. Suitable toxins and their corresponding fragments include diphtheria A chain, exotoxin A chain, ricin A chain, abrin A chain, curcin, crotin, phenomycin, enomycin, auristatins (e.g., auristatin E, or auristatin F), and the like. Targeting the therapeutic moiety to the α5β1 integrin expressed on the surface of a cancer cell not only serves to increase the local concentration of therapeutic moiety in the cancer afflicted area, but also serves to reduce deleterious side effects that may be associated with the therapeutic moiety.

Examples of chemotherapeutic agents that may used as therapeutic moieties with the anti-α5β1 antibodies of the present invention include, but are not limited to, adriamycin, doxorubicin, doxil, epirubicin, 5-fluorouracil, cytosine arabinoside ("Ara-C"), cyclophosphamide, thiotepa, busulfan, cytoxin, taxoids, e.g., paclitaxel (TAXOL™, Bristol-Myers Squibb Oncology, Princeton, N.J.), and doxetaxel (TAXOTERE™, Rhone-Poulenc Rorer), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

Alternatively, the method of the invention may be carried out wherein the chemotherapeutic agents disclosed above are administered in a formulation together with the anti-α5β1 antibody although not as a conjugate.

Cancer Indications

The present invention is directed to methods of killing cancer cells, inhibiting cancer cell proliferation and/or metastasis, by targeting α5β1 integrin on the cancer cell's surface with an antibody. Cancer is a physiological condition typically characterized by cells undergoing unregulated growth. Cancer includes all malignant neoplasms including but not limited to, carcinoma, lymphoma, blastoma, sarcoma, and leukemia. More particular examples of cancers that express α5β1 on the cell surface that may be targeted using the methods disclosed herein include, but are not limited to, bladder cancer, breast cancer, colon cancer, fibrosarcoma, lung cancer, metastatic melanoma, pancreatic cancer, prostate cancer, ovarian cancer, renal cell carcinoma and spleen cancer.

A tumor is a proliferating mass of cells lacking normal growth controls. A tumor may benign or malignant, and may include pre-cancerous, or cancerous, cells and tissues. Cancer cells typically form tumors as a cancer progresses. Tumor growth is accompanied by an increase in vascular density. This tumor neovasculature provides required nourishment that allows tumors to grow. The anti-angiogenic antibody therapeutics anti-α5β1 and anti-VEGF (VEGF=vascular endothelial growth factor) have demonstrated efficacy in impeding tumor growth in a variety of cancer models (see, e.g., Kim et al., *J. Clin Invest.*, 110(7):933-41 (2002); Ferrara, *Nat Rev Cancer*, 2(10):795-803 (2002)). The anti-α5β1 antibody, M200, has been shown to inhibit angiogenesis in vitro and in vivo in rabbit and monkey models of angiogenic ocular diseases (e.g., advance macular degeneration; see, U.S. patent application Ser. Nos. 10/724,274, filed Nov. 26, 2003, and Ser. No. 10/830,956, filed Apr. 23, 2004, each of which is hereby incorporated by reference herein).

The present invention is based on the surprising discovery that for many types of cancer α5β1 integrin is expressed on the surface of tumor epithelial cells (in addition to the endothelial cells of the tumor vasculature), and that targeted binding to this surface α5β1 with an antibody results in direct killing of these cancer cells. Consequently, cancers characterized by proliferating epithelial cells expressing α5β1 may be treated and/or targeted with anti-α5β1 antibodies even absent any tumor vasculature formation. Because this method of attacking and killing cancer cells is direct, it is amenable to very early stage treatment (i.e., prior to substantial tumor formation).

Patients most likely to benefit from the early-stage method of treatment would include, but are not limited to: 1) a patient who has had a pretumor diagnostic tests indicating a high probability of the development and/or presence of tumors (or microtumors); 2) a patient exposed to a very potent carcinogenic environment whose probability of tumor progression is high; and, 3) a patient whose genetic predisposition (e.g., as evidenced by a genetic marker for a cancer) makes the likelihood of cancer development high wherein the cancer cells express α5β1 on their surface. For example, a patient with a genetic predisposition for breast cancer (e.g., BRCA gene positive), or in whom some pretumor cancer marker has been detected (e.g., micro-metastases detected by PCR), will be particularly well-suited for the early-stage preventative direct cancer-cell killing method wherein a pharmaceutical composition of an anti-α5β1 antibody is administered.

Genes indicating an increased cancer predisposition, and tumor markers indicating a likelihood of developing a tumor may be found in the cancer biomedical literature and databases. In addition, lists of carcinogens and their exposure levels that greatly increase cancer risk are available in the biomedical literature well-known to those of ordinary skill in the art. One of ordinary skill may use these literature resources together with the well-known methods for detecting α5β1 integrin expression on cancer cells, disclosed below, to determine whether a subject may be amenable to the early-stage cancer treatment methods of the present invention. As described in Example 2 below, flow cytometry analysis reveals α5β1 integrin is expressed on the surface of cell lines originating from at least the following cancers: bladder cancer, breast cancer, colon cancer, fibrosarcoma, lung cancer, metastatic melanoma, pancreatic cancer, prostate cancer, ovarian cancer, and renal cell carcinoma.

Furthermore, the direct cancer cell killing method of the present invention may be particularly useful for treating cancers that express α5β1 but have not proven susceptible to anti-angiogenic approaches. Cancers in this category include, but are not limited to, bladder cancer, breast cancer, fibrosarcoma, renal cancer, pancreatic cancer, prostate cancer, ovarian cancer, lung cancer, and metastatic melanoma. In a particularly preferred embodiment, the methods of the present invention may be used to treat any of the above listed cancers wherein the patient exhibits refractory solid tumors. The anti-α5β1 antibody, M200 (volociximab) has demonstrated some efficacy for treating human patients with a variety of cancers exhibiting refractory solid tumors, including: colorectal cancer (CRC), melanoma (MEL), renal cell carcinoma (RCC), hepatocellular cancer (HCC), lung cancer (NSCLC), pancreatic cancer (PC), parotid cancer (PARO) and breast cancer (BC).

One of ordinary skill may determine those cancers that express α5β1 on the surface of tumor epithelial cells by using an anti-α5β1 antibody (e.g., IIA1 or M200) to probe tumor biopsy samples according to standard methods of immunohistochemistry. As described in Example 1 below, immunohistochemical (IHC) analysis of tumor biopsy samples taken from melanoma, lung, renal, pancreatic and breast cancer patients all showed α5β1 integrin expression on tumor epithelial cells. It is reasonable to expect that there other cancers will be found to express α5β1 on the surface of tumor epithelial cells using IHC (or other methods), and it is recognized that these cancers will be susceptible to the cancer cell kill method of the present invention.

In addition to IHC of tumor samples, cancer cell lines may be screened for α5β1 cell surface expression using an anti-α5β1 antibody and standard flow cytometry techniques well-known to those of ordinary skill in the art. As detailed in Example 2, below, flow cytometry screening revealed α5β1 expression on the surface of 21 well-known cancer cell lines. Based on this result, these cell lines are susceptible to direct cell killing using anti-α5β1 antibodies according to the methods of the invention. Furthermore, to the extent a cancer cell line is determined to express α5β1 on its surface, and the cell-line corresponds to, originated from, or is derived from, cancer cells present in a cancer patient, the methods of the present invention may be used to treat such a patient. For example, the NW231 cell line, which was found in Example 2 to express α5β1 integrin on its surface, originated from breast cancer tumors. Consequently, one of ordinary skill would immediately recognize that an anti-α5β1 antibody may be used to treat a breast cancer patient in accordance with the methods taught herein.

Compositions, Formulations and Administration of Antibodies

The anti-α5β1 antibodies useful in the methods of the present invention may be used in an isolated and purified form and directly contacted with cancers cells or tumors. Methods of purifying anti-α5β1 antibodies (e.g., IIA1, M200, and F200) are disclosed in U.S. patent application Ser. No. 10/724,274, filed Nov. 26, 2003, and Ser. No. 10/830,956, filed Apr. 23, 2004, each of which is hereby incorporated by reference herein. F200 may also be prepared as a Fab'-NAC fragment according to the methods disclosed in U.S. Pat. Appl. 60/583,127, filed Jun. 25, 2004, which is hereby incorporated by reference herein. The F200-Fab'-NAC exhibits increased stability in liquid and lyophilized formulations of the antibody. Purity and homogeneity may be determined using standard analytical chemistry techniques such as polyacrylamide gel electrophoresis or high performance liquid chromatography. An antibody that is the predominant species present in a preparation is considered to be substantially purified. For example, antibody solution that exhibits essentially one band in an electrophoretic gel is substantially purified. Preferably, the antibody used in the pharmaceutical compositions of the invention is at least 85% pure, more preferably at least 95% pure, and most preferably at least 99% pure.

In preferred embodiments, the direct cancer cell killing method is carried out wherein the purified anti-α5β1 antibodies are formulated into a pharmaceutical composition that is administered to a subject in a therapeutically effective amount. As used herein, "therapeutically effective amount" refers to the amount of a pharmaceutical formulation or composition that is sufficient to cure, alleviate, attenuate or at least partially arrest the cancer and/or its symptoms, and/or complications. Clinical methods for determining the therapeutically effective amount of an anti-α5β1 antibody for treatment of cancer are well-known to those of ordinary skill in the art and may be determined empirically using routine experimentation. For example, in the context of cancer treatment, a "therapeutically effective amount" is an amount capable of invoking one or more of the following effects: (1) inhibition, to some extent, of tumor growth, including, slowing down and complete growth arrest; (2) reduction in the number of cancer cells; (3) reduction in tumor size; (4) inhibition (i.e., reduction, slowing down or complete stopping) of cancer cell infiltration into peripheral organs; (5) inhibition (i.e., reduction, slowing down or complete stopping) of cancer cell metastasis; (6) enhancement of anti-cancer immune response, which may, but does not have to, result in the regression or rejection of a tumor; and/or (7) relief, to some extent, of one or more symptoms associated with the disorder.

The pharmaceutical compositions for administration will commonly comprise an anti-α5β1 antibody dissolved in a pharmaceutically acceptable carrier or excipient, preferably an aqueous carrier. Acceptable carriers, excipients, or stabilizers, for the pharmaceutical composition are those which are nontoxic to the cell or mammal being exposed thereto at the dosages and concentrations employed. Examples of physiologically acceptable carriers include buffers such as phosphate, citrate, and other organic acids, antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrans; chelating agents such as EDTA; sugar alcohols such as mannitol or sorbitol; salt-forming, counter-ions such as sodium; and/or nonionic surfactants such as TWEEN®, polyethylene glycol (PEG), and PLURONICS™. A variety of aqueous carriers can be used, e.g., buffered saline and the like. These solutions should sterile and generally free of undesirable matter. The pharmaceutical compositions may be sterilized by conventional, well known sterilization techniques.

The pharmaceutical compositions also may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and other pharmaceutically acceptable salts, which is meant to include both acid and base addition salts. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. The concentration of antibody in these formulations can vary widely, and will be selected primarily based on fluid volumes, viscosities, body weight and the like in accordance with the particular mode of administration selected and the patient's needs (e.g., "Remington's Pharmaceutical Science" (15th ed., 1980) and Goodman & Gillman, "The Pharmacologial Basis of Therapeutics" (Hardman et al., eds., 1996)).

In a preferred embodiment of the methods of the present invention, the anti-α5β1 antibody is formulated as a pharmaceutical composition comprising a solution of between about 1.0 mg/mL and 15.0 mg/mL antibody, about 22 mM to 28 mM citrate, about 135 mM to 165 mM Sodium Chloride, 0.04%-0.06% Polysorbate (TWEEN™) 80, at a pH of 5.5 to 7.5. Preferably, the pH range of the liquid formulation is between about pH 6.0 and pH 7.0, and most preferably between about pH 6.3 and pH 6.7. In a particularly preferred embodiment the pharmaceutical composition comprises a solution of about 10.0 mg/mL antibody, about 25 mM citrate, about 150 mM sodium chloride, about 0.05% polysorbate (TWEEN®) 80, at a pH of about 6.5. In other embodiments, the above anti-α5β1 antibody pharmaceutical composition may further comprise a chemotherapeutic agent, or alternatively, may be administered to a patient together with a pharmaceutically effective amount of another chemotherapeutic agent.

Preferably the liquid formulation of the pharmaceutical composition is a stable, colorless, or clear to slightly opalescent solution exhibiting no more than 10%, and preferably 5% or less of degaded antibody monomer as measured by SEC-HPLC. Preferably, no more than 10%, and preferably 5% or less of hydrolysis clipping is observed, and no more than 10%, and preferably 5% or less of antibody aggregation is formed. Preferably, the concentration, pH and osmolality of the formulation have no more than ±10% change. Potency is within 70-130%, preferably 80-120% of the control.

The administration of the pharmaceutical compositions comprising anti-α5β1 antibodies to a subject may be carried in a variety of ways, including, but not limited to, orally, subcutaneously, intravenously, intranasally, topically, transdermally, intraperitoneally, intramuscularly, intrapulmonary, vaginally, rectally, intraocularly, intraventricularly, or intrathecally. It is well recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The pharmaceutical compositions may be administered in a variety of unit dosage forms depending upon the method of administration. For example, unit dosage forms suitable for oral administration include, but are not limited to, powder, tablets, pills, capsules and lozenges.

The exact dosage to be used in a particular embodiment of the method of the invention will depend on the purpose of the treatment, and may be ascertained by one skilled in the art using well-known techniques (e.g., Ansel et al., "Pharmaceutical Dosage Forms and Drug Delivery;" Lieberman, "Pharmaceutical Dosage Forms" (vols. 1-3, 1992), Dekker, ISBN 0824770846, 082476918X, 0824712692, 0824716981; Lloyd, "The Art, Science and Technology of Pharmaceutical Compounding" (1999); and Pickar, "Dosage Calculations" (1999)). As is known in the art, adjustments for cancer degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

In one embodiment of the methods of the present invention, a pharmaceutical compositions comprising an anti-α5β1 antibody is administered to a patient based on the weight of antibody (in mg) per patient body weight (in kg). Thus, preferred dose levels include at least about 0.5 mg/kg, 1.0 mg/kg, 2.5 mg/kg, 5.0 mg/kg, 10.0 mg/kg, and 15 mg/kg. Preferably, the dose is administered to the patient as an intravenous infusion over 1 hour. Additional doses may be administered over an extended time period such that a steady state serum concentration is established in the patient. For example, an infusion of 10 mg/kg may be administered once a week over the course of a year.

In one preferred embodiment, the anti-α5β1 antibody dosing level and schedule are selected to ensure that the dose produces a maximum serum concentration below the safe mean peak serum concentrations seen in pharmacokinetic studies carried out in monkeys (e.g., cynomolgus). For example, in cynomolgus monkeys, the mean peak level of M200 at a dose of 50 mg/kg after 4 weekly doses was 1862 µg/mL (range: 1000-2606 µg/mL). The monkeys showed no toxicity at these serum concentrations. In addition, or alternatively, a dose may be selected so that the trough serum level is >1 µg/mL, the concentration that produces 80% inhibition of binding of α5β1 to fibronectin in an in vitro activity assay.

In accordance with one embodiment of the methods of therapeutic cancer cell killing of the present invention, a pharmaceutical composition comprising an anti-α5β1 antibody is administered to a patient intravenously at a fixed dosage, typically about 0.1 to 10 mg per patient per day. In embodiments where the pharmaceutical composition is administered to a secluded site, such as into a body cavity or into a lumen of an organ, and not into the blood stream, fixed dosages from 0.1 mg up to about 100 mg per patient per day may be used. Substantially higher dosages are possible for embodiments where topical administration is desired. Actual methods for preparing parenterally administrable compositions will be known or apparent to those skilled in the art, e.g., "Remington's Pharmaceutical Science," and Goodman and Gillman, "The Pharmacologial Basis of Therapeutics," supra.

The pharmaceutical compositions employed in the cancer cell killing method of the invention may be administered as part of a therapeutic or prophylactic treatment. In a therapeutic method, the pharmaceutical composition is administered to a patient already suffering from a cancer in an amount sufficient to cure, or at least partially arrest the progress of the disease and its complications. Generally, in a therapeutic treatment context, the progress of the therapy may be measured as decrease in tumor size or a decrease in the rate of tumor growth. An amount adequate to accomplish this is defined as a "therapeutically effective dose." Amounts effective for this use will depend upon the severity of the cancer and the general state of the patient's health. Single or multiple administrations of the pharmaceutical compositions may be employed depending on the dosage and frequency tolerated by the patient.

A early-stage treatment method is directed to preventing or slowing the development of cancer in a subject that is suspected of developing the disease, or in the very early stage of the disease. The particular dose required for an early-stage treatment will depend upon the medical condition and history of the patient, the particular cancer being prevented, as well as other factors such as age, weight, gender, administration route, efficiency, etc. An early-stage treatment method also may be used prophylactically, e.g., in a patient who has previously had cancer to prevent a recurrence of the cancer, or in a patient who is suspected of having a significant likelihood of developing cancer. For example, a patient with a genetic predisposition for breast cancer, in whom some pre-tumorous cancer marker has been detected (e.g., micro-metastases detected by PCR), will be particularly well-suited for the early-stage treatment method.

In an alternative embodiment of the present invention, the direct cancer cell killing method may be carried out wherein a chemotherapeutic agent is administered in addition to the anti-α5β1 antibody. Typical chemotherapeutic agents useful in this embodiment are disclosed supra. This combination therapy method may be particularly preferred in an early-stage, or prophylactic treatment context where the patient lacks fully developed disease symptoms. At this early stage, or in a preventative context, many patients may not agree to undergo the toxic side effects that accompany the use of a standard chemotherapy agent alone. By administering a lower dosage of the standard chemotherapeutic together with a relatively non-toxic anti-α5β1 antibody, the cancer may be treated prophylactically, or at a very early-stage, with a regimen that is effective yet much more tolerable for the patient.

The following examples are intended to illustrate but not limit the invention disclosed herein.

EXAMPLES

Example 1

α5β1 Expression on Tumor Samples Detected by IHC

Tumor biopsy samples taken from melanoma, lung, renal, pancreatic and breast cancer patients were surveyed for α5β1 integrin expression by immunohistochemistry (IFC).

Materials and Methods

Frozen tissue samples (obtained from the Mayo Clinic or Cleveland Clinic), were frozen in optimal cutting temperature (OCT) compound and stored at −70° C. Cryostat tissue sections (7 μm) were fixed in 75% acetone/25% ethanol for 1 minute. Samples were incubated with either the anti-α5β1 mouse antibody IIA1 (5 μg/ml) or control mouse IgG1 (anti-trinitrophenyl, ATCC hybridoma clone 1B7.11) for 30 minutes. Antibody binding was detected using the biotinylated secondary antibody, goat-anti-mouse IgG (3 μg/ml, 30 minutes; Jackson ImmunoResearch), and developed using the Vectastain Elite ABC Kit (Vector Laboratories) and stable DAB (diaminobenzidine and $H_2O_2$; Research Genetics). Staining was performed using the DAKO Autostainer at room temperature.

Results

As shown in Table 1, nearly all of the tumor sections analyzed stained positive for α5β1 on the tumor vasculature. Surprisingly, a significant proportion of tumor samples also exhibited positive staining for α5β1 integrin expression on the tumor epithelium itself. These results indicate that an anti-α5β1 antibody will directly target cancer cells in addition to the invading neovasculature.

TABLE 1

IHC results for tumor samples stained with anti-α5β1 antibody IIA1

| Tumor type | Tumor Vasculature | | | | | Tumor Epithelium | | | | |
|---|---|---|---|---|---|---|---|---|---|---|
| (# samples) | Neg | 1+ | 2+ | 3+ | 4+ | Neg | 1+ | 2+ | 3+ | 4+ |
| Renal (n = 39) | 2 | 2 | 13 | 18 | 4 | 27 | 8 | 4 | 0 | 0 |
| Pancreatic (n = 32) | 0 | 1 | 17 | 12 | 2 | 15 | 2 | 7 | 7 | 1 |
| Lung (n = 39) | 0 | 1 | 0 | 28 | 1 | 19 | 14 | 3 | 2 | 1 |
| Colon (n = 21) | 2 | 2 | 3 | 8 | 6 | 19 | 0 | 1 | 1 | 0 |
| Melanoma (n = 19) | 3 | 0 | 2 | 13 | 1 | 13 | 5 | 1 | 0 | 0 |
| Ovarian omental mets (n = 4) | 0 | 0 | 1 | 3 | 0 | 2 | 2 | 0 | 0 | 0 |
| Bladder (n = 8) | 0 | 0 | 4 | 3 | 1 | 5 | 2 | 1 | 0 | 0 |

Example 2

α5β1 Expression on Cancer Cell Lines Detected by Flow Cytometry

A panel of 24 cancer cell lines was surveyed by flow cytometry for α5β1 integrin expression on the cell surface. As shown in Table 2, these 24 cell lines originated in a variety of different cancers including: bladder, breast, colon, fibrosarcoma, lung, melanoma, pancreas, prostate, ovarian, renal, and spleen.

Materials and Methods

Cells were removed with 5 mM EDTA in Tris-HCl (pH 8.0) and blocked by centrifugation in Hank's balanced salt solution containing 3% heat inactivated FBS, 1% normal goat serum (Sigma) and 1% BSA at 4° C. for 5 minutes. Cells were incubated for 30-60 minutes at 4° C. with the mouse anti-α5β1 antibody, IIA1 (10 μg/ml) in FACS buffer (PBS containing 0.1% BSA). Excess monoclonal antibody was removed by centrifugation and cells were washed two times with FACS buffer prior to resuspending in PE-anti-mouse IgG (H+ L) antibody (Southern Biotech, 1:400 dilution) for 30-60 minutes at 4° C. After washing cells were re-suspended in FACS buffer containing propidium iodide (1 μg/ml). Mean fluorescence intensity (MFI) was measured on a FACSCalibur (Becton Dickinson). Background MFI was ~5.

Results

As shown in Table 2, significant detectable surface expression of α5β1 integrin was observed for 21 of the 24 cell lines assessed. Three cancer cell lines CHL-1, COLO 357 and C32 exhibited MFI values that were very close to background indicating little or no surface expression of α5β1 integrin. The 21 cell lines expressing α5β1 integrin on their surface should be vulnerable to direct cell killing by an anti-α5β1 antibody. In addition, the cancer from which these cell lines were originated may be susceptible to treatment with an anti-α5β1 antibody therapeutic.

TABLE 2

Results for FACS analysis of various cancer cell lines with IIA1, and in vitro proliferation assay with M200.

| | | α5β1 Surface Expression | % Growth Inhibition | |
|---|---|---|---|---|
| Cell Line | Cancer of Origin | (MFI) | −Serum | +Serum |
| A549 | lung | 71.41 | 40 | 0 |
| H460 | lung | 87.5 | 40 | 0 |
| SW839 | renal | 65.8 | 30 | 0 |
| MIA PACA-2 | pancreas | 61.9 | 20 | 0 |
| HCT-116 | colon | 42.5 | 15 | 0 |
| 786-0 | renal | 144.4 | 10 | 0 |
| EKVX | lung | 36.7 | 10 | 0 |
| SW1990 | spleen | nd[1] | 10 | 0 |
| SN12C | renal | 129.1 | 5 | 0 |
| A498 | renal | 67.1 | 5 | 0 |
| A375 | melanoma | 156.1 | 5 | 0 |
| A2058 | melanoma | 36.2 | 0 | 0 |
| CHL-1 | melanoma | 6.8 | 0 | 0 |
| TK-10 | renal | 36.6 | 0 | 0 |
| COLO 357 | pancreas | 7.8 | 0 | 0 |
| HT144 | melanoma | 102.1 | 0 | 0 |
| C8161 | melanoma | 122 | 0 | 0 |
| HT1376 | bladder | 111.9 | 0 | 0 |
| DU145 | prostate | 87.5 | 0 | 0 |
| UACC-62 | melanoma | 88.5 | 0 | 0 |
| HT1080 | fibrosarcoma | 421.7 | 0 | 0 |
| ES-2 | ovarian | 132.8 | 0 | 0 |
| CAPAN-1 | pancreas | nd[1] | 0 | 0 |
| CAPAN-2 | pancreas | nd[1] | 0 | 0 |
| ASPC-1 | pancreas | nd[1] | 0 | 0 |
| C32 | melanoma | 5.7 | 0 | 0 |
| LOX | melanoma | 261.6 | 40[2] | 35 |
| NW231 | breast | 132.2 | 10[2] | 35 |

[1] nd = not determined
[2] Values for % growth inhibition were determined in a 2-day rather than 4-day assay.

Example 3

M200 Inhibition of In Vitro Cancer Cell Proliferation

A panel of 28 cancer cell lines was assessed for sensitivity to the chimeric anti-α5β1 antibody M200 in a cell proliferation assay in the presence or absence of serum.

Materials and Methods

Cancer cell lines were plated at a density of 2500 cells/well in 96-well plates in IMDM with supplements in the presence or absence of 10% FBS. At the time of plating, cells were challenged with various concentrations M200 or a non-function blocking anti-α5 antibody, VC5. Four days later, cell viability was assessed by the CellTiter 96 AQueous Non-Radioactive Cell Proliferation Assay (Promega) according to the manufacturer's instructions. All growth studies were done at least 3 times in triplicate.

Results

As shown in Table 2, M200 inhibited growth of thirteen cancer cell lines in the absence of serum and two cell lines in the presence of serum. Two of the cell lines, LOX and NW231 were found to be sensitive to M200, under both conditions. Based on these results, the cancers from which these cell lines originate (melanoma and breast) are likely to respond to treatment with M200.

Example 4

In Vivo Inhibition of Tumor Cell Proliferation in NW231 and LOX Xenograft Models NW231 and LOX cells were grown as orthotopic xenografts in SCID mice and challenged with the anti-α5β1 antibodies M200 and IIA1 by intraperitoneal injection.

Materials and Methods

Immune compromised mice CB-17 SCID (strain C.B-Igh1/IcrTac-Prkdc) were obtained from Taconic Farms (Germantown, N.Y.). Studies were initiated using female mice between the ages of 6-10 weeks (~20 grams in weight). Animals were pre-dosed with M200, IIA1 or control IgG intraperitoneally at a dose of 10 mg/kg 1 hour prior to NW231 inoculation ($1 \times 10^7$ cells in IMDM) into the mammary fat pad. Dosing continued for 3 weeks at a frequency of 3 times/week at 10 mg/kg. Tumor volume was measured twice weekly by caliper and calculated by π/6×length×width×height. Clinical and mortality observations were performed daily according to IACUC regulations.

Results

IIA1, was found to reproducibly inhibit both NW231 and LOX xenograft tumor growth in this model. M200 was not found to reproducibly inhibit tumor growth in these models. Since IIA1 does not recognize mouse α5β1 in the xenograft tumor vasculature, the entire inhibitory effect of IIA1 on tumor growth may be attributed to a direct anti-proliferative effect on the cancer cells of the tumor.

Example 5

IIA1 in Combination with DOXIL® Prevents Tumor Establishment in an In Vivo NW231 Xenograft Model The following experiment was conducted in order to determine the efficacy of the anti-α5β1 integrin antibody, IIA1 in combination with the chemotherapeutic agent, DOXIL®, for preventing establishment of human NW231 tumors in vivo. DOXIL® is a liposome encapsulated formulation of doxorubicin HCl, a cytotoxic anthracycline antibiotic isolated from *Streptomyces peucetius*. The NW231 cell line originated from breast cancer and is considered a good model for studying treatments for breast cancer.

Materials and Methods

Four to six week old female SCID mice obtained from Taconic Farms and maintained in micro-isolator cages were inoculated in the mammary fat pads with $1 \times 10^7$ NW231 cells. Animals received either TIB control (n=20) or M200 (n=20) at 5 mg/kg for the first injection at the time of tumor cell inoculation. Subsequent treatments were at 0.7 mg/kg per injection. DOXIL® treatment was commenced 5 days post tumor cell inoculation. Chemotherapeutic doses were at 4 mg/kg for the first injection and at 2 mg/kg for subsequent injections. Reagents were delivered by intraperitoneal injection for four doses. Tumor volume was measured twice weekly and clinical and mortality observations were performed daily according to IACUC regulations.

Results

IIA1 treatment exhibited a significant effect in slowing the establishment of the NW231 tumors in mice. At 24 days post-implant of NW-231 tumors, the mean tumor volume of control TIB treated xenografts had increased in an exponential fashion to ~425 mm$^3$ whereas the IIA1 treated xenografts had increased to a mean volume of ~175 mm$^3$.

DOXIL® treatment by itself also exhibited a significant effect in preventing tumor establishment. For the DOXIL® alone treated xenografts, mean tumor volume initially increased to only ~25 mm$^3$ during the first 45 days post-implant, and then increased gradually up to ~275 mm$^3$ by day 74.

Treatment of mice with the combination therapy of IIA1 and doxil had an even greater inhibitory effect on the rate of tumor establishment compared to either treatment alone. For the IIA1 plus DOXIL® treated xenografts, mean tumor volume remained near zero out to day 54, then increased gradually but only up to ~125 mm$^3$ by day 74. These results indicate increased efficacy (i.e., a combined tumor inhibitory effect) in vivo for the combined treatment of an anti-α5β1 antibody, IIA1 and a chemotherapeutic agent, DOXIL®.

Example 6

M200 Efficacy Measured in an VX2 Rabbit Tumor Model

Although M200 does not cross react with mouse or rat α5β1 integrin, it does recognize α5β1 integrin found in rabbit. Thus, the rabbit VX2 carcinoma may represent a good model for determining the in vivo direct cancer cell killing efficacy of M200. VX2 is a widely accepted rabbit model for studies on treatment of primary tumors of various locations (see e.g., Chen J G, et al, Lab Anim. 2004 January; 38(1):79-84; Purdie, T G et al, Phys Med Biol. 2001 December; 46(12): 3161-75); Geschwind, J H, et al, Cancer Res. 2002 July 62(1): 3909-3913).

A. M200 VX2 Pilot Study

An initial Pilot Study was carried out to determine the general parameters for conducting the M200 efficacy study in the rabbit VX2 tumor model.

Tumor Inoculation

Rabbits were inoculated on Day 0 with a cell suspension (100 μl) subcutaneously (left hind limb), and intramuscularly at a depth of about 3 mm (right hind limb). Intramuscular inoculation was carried out as follows. With the rabbit under ketamine/isoflurane anesthesia, a ~2 cm incision was made parallel to the right femur with a scalpel on the anterior, lateral aspect of the femoral axis, ~⅓ of the total femur length distally from the femoral-pelvic (hip) joint. Muscle groups were separated to create a ~0.5 cm deep cavity. One VX2 tumor fragment from a donor animal was placed into the cavity. Skin was securely closed with sterile surgical staples or sutures and a topical antibiotic was applied to the wound site.

Tumor Measurements

Starting on Day 5, tumor dimensions (Length, Width and Height) were measured in millimeters via electronic vernier calipers connected to a laptop computer at a minimum frequency of twice weekly. For consistency, the same trained technician performed the tumor measurements throughout the course of the study. Tumor volume was calculated using the formula: Length×Width×Height×0.52. Upon animal termination, tumors were carefully excised, trimmed and weighed. In addition, animals were weighed a minimum of once weekly. Representative samples of each tumor were preserved in sample cassette in formalin or OCT and flash frozen in liquid nitrogen.

In Vivo Passaging of VX2 Tumors

The VX2 tumors used in both the Pilot and M200 efficacy study were maintained by in vivo passaging on a monthly basis. Either a cell suspension (100 µl) or pieces of tumor (~5-10 mm$^3$) were used for intramuscular inoculation in each hind limb. The animals and tumors were visually monitored and tumors removed before reaching 2 cm in diameter for in vivo passaging. In vivo passage was carried out by sacrificing the animal, removing the tumor, and processing the tumor into 5-10 mm$^3$ pieces. The pieces were then re-implanted into the next group of 2 rabbits.

IHC Analysis of VX2 Tumors from M200 Treated Rabbits

M200 was administered intravenously at 10 mg/kg dosage to a tumor-bearing rabbit and the tumor was excised 1 hour later. Tumor sections were stained with either: (i) an anti-human secondary antibody specific for tumor bound M200; (ii) IIA1 followed by an anti-mouse secondary to detect total α5β1; or (iii) a control IgG and anti-mouse secondary.

Results

Both the subcutaneous tumors and the intramuscular tumors were found to be accessible to M200 injected intravenously into the animals, as assessed by IHC. IHC analysis of the stained sections revealed high levels of α5β1 expression both in VX2 tumor cells and rabbit tumor vasculature.

B. M200 VX2 Efficacy Study

Based on the pilot study IHC results, the VX2 rabbit model was used to assess M200 efficacy in vivo.

Methods

Rabbits (30 total) were inoculated, either subcutaneously or intramuscularly with either a VX2 cell suspension (100 µl) or pieces of tumor (~5-10 mm$^3$). The test group of 20 was treated with M200 at 10 mg/kg intravenously, twice weekly for 3 weeks. The control group of 10 animals was treated with a control IgG delivered by the same method as the M200. Tumor measurements, termination, weighing, tumor preservation and study duration were carried out according to the methods described above for the Pilot Study. In addition, one milliliter of blood was taken from an ear vessel on a weekly basis for serum analysis.

Results

A strong correlation was observed between inhibition of tumor growth and circulating levels of M200 in the animals. In general, when the levels of M200 were maintained at or above 50 µg/mL, then tumor growth was inhibited. Since M200 is immunogenic in rabbits, some of the test group rabbits generated an immune response to M200 as early as two weeks following M200 administration, and eventually all of the animals were found to seroconvert. In the test group animals that generated an anti-idiotype response resulting in the clearance of M200 (i.e. M200<50 µg/mL at day 14), larger tumor growth was observed. Thus, the results observed with the VX2 carcinoma model indicate that M200 is able to inhibit tumor growth in a robust in vivo oncology model.

Example 7

M200 and IIA1 Efficacy in a SCID Mouse VX2 Xenograft Model

As described in Example 6, M200 exhibited efficacy in a rabbit VX2 carcinoma model. A further measure of the direct cancer cell killing ability of M200 and IIA1 was carried out in a SCID mouse VX2 xenograft model. Because M200 and IIA1 do not recognize mouse α5β1 integrin present on the VX2 xenograft tumor vasculature, any inhibitory effect on VX2 xenograft tumor growth may be attributed to a direct anti-proliferative effect that M200 and IIA1 has on VX2 cancer cells.

Materials & Methods

Immune compromised mice CB-17 SCID (strain C.B-Igh1/IcrTac-Prkdc) were obtained from Taconic Farms (Germantown, N.Y.). Studies were initiated using female mice between the ages of 6-10 weeks (~20 grams in weight). Animals were pre-dosed with M200, IIA1, or control IgG intraperitoneally at a dose of 10 mg/kg one hour prior to VX2 inoculation (1×10$^7$ cells in Iscove's Modified Dulbecco's Medium) into the mammary fat pad. Dosing was continued for 3 weeks at a frequency of 3 times/week at 10 mg/kg. Tumor volume was measured twice weekly by caliper and calculated by π/6×length×width×height. Clinical and mortality observations were performed daily according to IACUC regulations.

Results

Dosing with M200 or IIA1 did not correlate with a decreased rate of VX2 tumor growth or an overall decreased tumor size versus the mice dosed with control IgG. These results suggest that neither M200 and IIA1 are able to directly kill VX2 cells in the mouse xenograft model.

Example 8

Phase I Dose-Escalation Study of M200 in Human Patients with Refractory Solid Tumors A. Overview A two-part Phase I open-label study was carried to determine the effects of treatment with up to 6 dose levels, from 0.5 mg/kg to 15.0 mg/kg of M200 (volociximab) in 21 human patients with a variety of refractory solid tumor types. The total duration of treatment for the first part was 6 weeks with physical assessments through 45 days after the last dose. The second part was an extension study wherein 6 of the 11 patients who exhibited a stable disease response in the first part received continued M200 dosing for up to 52 weeks.

B. Study Parameters and Protocols

1. Patient Selection

Patients selected for the study had to meet the following inclusion/exclusion criteria:

a. At least one measurable lesion on routine computed tomography (CT) imaging or magnetic resonance imaging (MRI).

b. An estimated survival of ≧3 months; Eastern Collaborative Oncology Group (ECOG) performance status≦2;
c. No central nervous system (CNS) tumors or metastasis (documented at screening by head imaging);
d. No major surgery within 4 weeks prior to entry;
e. No minor surgery within one week prior to entry; no chemotherapy, immunotherapy, or radiotherapy within 4 weeks prior to entry;
f. No active bleeding disorder or thromboembolic events;
g. No other clinically significant or unstable medical condition.
h. Patients who had previously received murine or chimeric MAb therapy were required to test negative in screening for anti-M200 antibodies (i.e., crossreactive human-anti-murine-antibody [HAMA] or human-anti-chimeric antibody [HACA]).

A total of 22 patients were enrolled in the study. Tumor types of the 22 patients included: colorectal (4 patients; CRC), melanoma (4 patients; MEL), renal cell carcinoma (3 patients; RCC), esophageal (2 patients; EC), hepatocellular (2 patients; HCC), lung (1 patient; NSCLC), prostate (1 patient; PRO), thyroid (1 patient; THY), pancreatic (2 patients; PC), parotid (1 patient; PARO) and breast (1 patient; BC). Twenty-one of the 22 patients were treated, and 20 of the 21 treated patients completed all 5 doses plus follow-up through day 45. The 21 treated patients (12 male, 9 female) had a median age of 59 years (range 29-81), and a mean Eastern Collaborative Oncology Group (ECOG) score of 1 (range 0-2).

2. Selection of M200 Dosing Levels and Schedule

Dosing levels and schedule were chosen to ensure that the highest dose (15.0 mg/kg) would produce maximum serum concentrations well below the safe mean peak serum concentrations seen in cynolmolgus monkeys, and so that the trough serum levels for doses of ≧1.0 mg/kg would produce serum concentrations>1 μg/mL, the concentration that produces 80% inhibition of binding of α5β1 to fibronectin in an in vitro activity assay.

The dosing levels and schedule used in the study were as follows. M200 was administered to the 21 patients on days 1, 15, 22, 29, and 36. The dosing levels and numbers of patients per level were: 0.5 mg/kg (1 patient), 1.0 mg/kg (2 patient), 2.5 mg/kg (3 patients), 5.0 mg/kg (3 patients), 10.0 mg/kg (6 patients) and 15 mg/kg (6 patients). The dose was administered as an intravenous infusion over 1 hour. The first and second doses were separated by a two week period to allow sampling for single-dose pharmacokinetic data. The real-time PK measurements performed following the first dose were used to predict each patient's peak serum concentration following the fifth dose. If the predicted peak serum concentration following the fifth dose was <750 μg/mL, the patient received all 5 doses of M200. The remaining 3 doses were given weekly and followed by a 45-day evaluation period.

Human serum concentrations of M200 were predicted based on the above dosing scheme and applying the same range of variabilty that was observed in the cynomolgus monkeys (i.e., 54%-140% of the mean). At the highest dose in humans (15.0 mg/kg), the mean peak after 5 doses was predicted to be 592 μg/mL with the range of variability in humans predicted as 320 to 829 μg/mL. Table 3, was compiled using PK data from the monkey studies to predict the peak and tough serum concentrations (Cmax and Cmin, respectively) for each dose at each dose level in humans.

TABLE 3

Estimated Peak and Trough Serum Levels of M200 in Humans

| Dose Level | Dose (mg/kg) | PK Value[a] | Dose Number 1 | 2 | 3 | 4 | 5 |
|---|---|---|---|---|---|---|---|
| 1 | 0.5 | Cmax | 11 | 11 | 12 | 13 | 13 |
|   |   | Cmin[b] | 1.5 | 1.6 | 2 | 2.1 | 2.2 |
| 2 | 1.0 | Cmax | 22 | 22 | 25 | 26 | 26 |
|   |   | Cmin | 3 | 3 | 4 | 5 | 5 |
| 3 | 2.5 | Cmax | 54 | 57 | 64 | 67 | 68 |
|   |   | Cmin | 9 | 10 | 13 | 14 | 15 |
| 4 | 5.0 | Cmax | 108 | 114 | 132 | 141 | 147 |
|   |   | Cmin | 20 | 24 | 33 | 39 | 43 |
| 5 | 10.0 | Cmax | 216 | 236 | 282 | 317 | 346 |
|   |   | Cmin | 51 | 66 | 101 | 131 | 156 |
| 6 | 15.0 | Cmax | 324 | 366 | 450 | 524 | 592 |
|   |   | Cmin | 91 | 126 | 200 | 268 | 332 |
|   |   | Cmax range (54-140%) | 175-453 | 197-512 | 243-629 | 283-733 | 320-829 |

[a]Values expressed in μg/mL.
[b]Calculated for values expected 1 week after first dose.

Based on the above table, the terminal half-life in humans at 15.0 mg/kg was predicted to be about 13 days, and less for lower doses. M200 accumulation in serum was predicted to be substantive at dose levels≧5.0 mg/kg, with a steady state concentration reached within 4 weeks for all doses<10.0 mg/kg and within 5 weeks for doses≧10.0 mg/kg.

3. M200 Formulation and Administration

M200 bulk biologic was manufactured in accordance with current Good Manufacturing Practices (cGMP). The composition of the M200 formulation used in the present study was 10 mg/mL M200, 25 mM Citrate, 150 mM Sodium Chloride, 0.05% Polysorbate (TWEEN®) 80, with a pH of 6.5. This formulation is a sterile, colorless, clear-to-slightly opalescent, preservative-free liquid for I.V. use. Each 20-mL single-use vial was filled to deliver 15 mL of M200 at 10.0 mg/mL. Each 10-mL single-use vial was filled to deliver 10 mL of M200 at 10.0 mg/mL. Intact vials were stored in a refrigerator at 2° C. to 8° C. (36° F.-46° F.) and maintained without freezing or shaking.

Once prepared, the M200 was administered within 6 hours if stored at room temperature (25° C.) or 48 hours if refrigerated (between 2-8° C.). After that time, the prepared solution was discarded.

The appropriate dose of M200 to be administered to the patient was calculated by multiplying the patient's weight (kg) by the appropriate dose level (mg/kg) for the patient. The patient's pre-dose weight on Study Day 1 was used to calculate the dose throughout the study. For patients enrolled in the 0.5 mg/kg through the 10.0 mg/kg dose cohorts and for patients weighing≦80 kg enrolled in the 15.0 mg/kg dose cohort, the dose was administered in a fixed total volume of 120 mL over one hour.

Although 120 mL of the diluted study drug was administered to the patient, the infusion bag was prepared to contain a total of 150 mL. The additional 30 mL was used to prime the infusion line and was not be administered to the patient. Thus, the total dose of study drug placed into the infusion bag was the patient's dose (i.e., the patient's weight (kg)×dose level [mg/kg] multiplied by 1.25). The total volume in the infusion bag was brought up to 150 mL by adding Sodium Chloride for Injection, USP (0.9%).

Patients weighing >80 kg enrolled in the 15.0 mg/kg dose cohort had their dose administered in a fixed total volume of 180 mL over one hour. Although 180 mL of the diluted study drug was administered to the patient, the infusion bag was prepared to contain a total of 210 mL. The additional 30 mL was used to prime the infusion line and was not be administered to the patient. Thus, the total dose of study drug placed into the infusion bag was the patient's dose (i.e., the patient's weight (kg)×dose level [mg/kg] multiplied by 1.167). The total volume in the infusion bag was brought up to 210 mL by adding Sodium Chloride for Injection, USP (0.9%).

The pre-filled infusion line was attached directly to the patient's IV access (e.g., heparin lock). The infusate was administered at a rate of 2 mL/min (or 3 mL/min for 15.0 mg/kg cohort patients weighing>80 kg) over one hour using an infusion pump.

4. Primary Endpoints and Adverse Events

The study endpoints included maximum tolerated dose, dose-limiting toxicity, safety profile, immunogenicity, pharmacokinetics (PK), monocyte saturation (monocytes express the $\alpha 5\beta 1$ receptor), and tumor response based on Response Evaluation Criteria in Solid Tumors (RECIST) criteria (see, Therasse P, et al., "New guidelines to evaluate the response to treatment in solid tumors," *Journal of the National Cancer Institute*, 92(3):205-216 (2000), which is hereby incorporated by reference herein in its entirety).

Adverse events were graded using the National Cancer Institute (NCI) Common Terminology Criteria for Adverse Events (CTCAE), version 3.0. Dose-limiting toxicity was defined as any Grade-3 or Grade-4 adverse event, excluding scheduled hospitalizations or elective surgeries. Grade-3 or Grade-4 adverse events thought to be unrelated to M200 were excluded where appropriate following a review with the medical monitor and regulatory agencies.

Patient evaluations during the study included the following:

a. Screening (within 14 days of study entry) of: medical history and physical examination, ECOG performance status, routine chemistry panel, complete blood count (CBC) with differential and platelets, sensitive C-reactive protein (CRP), urinalysis with microscopic analysis (UA/micro), electrocardiogram (ECG), chest radiograph (CXR), disease-directed body CT or MRI, urine pregnancy test within 48 hours prior to dosing, and coagulation studies (prothrombin [PT] and partial thromboplastin time [PTT]), anti-M200 antibodies (i.e., to detect cross-reactive HAMA or HACA) for patients who previously received murine or chimeric antibodies, head CT for patients with tumors that commonly metastasize to brain or CNS, and, in some patients, a biopsy to evaluate tumor vessel vascularity.

b. On-study laboratory evaluations: routine chemistry panel, urate, serum amylase, CBC with differential and platelets, UA/micro.

c. Routine disease-directed radiographic imaging (e.g., CT scanning) before and after treatment with M200 was used to evaluate tumor response using uni-dimensional, RECIST criteria. Target lesions were selected on the basis of their size (lesions with the longest diameter (LD)) and their suitability for accurate repetitive measurements (either by imaging techniques or clinically). A sum of the LD for all target lesions was calculated and reported as the baseline sum LD. The baseline sum LD was used as reference by which to characterize the objective tumor response. The following response criteria for the target lesions was used to assess the best overall response.

Complete Response (CR): Disappearance of all target lesions confirmed by repeat imaging 25 to 28 days after CR first documented.

Partial Response (PR): At least a 30% decrease in the sum of LD of target lesions, taking as reference the baseline sum LD, confirmed by repeat imaging 25 to 28 days after PR first documented.

Stable Disease (SD): Neither sufficient shrinkage to qualify for PR nor sufficient increase to qualify for PD, taking as references the smallest sum LD.

Progressive Disease (PD): At least a 20% increase in the sum of LD of target lesions, taking as reference the smallest sum LD recorded since treatment started, or the appearance of one or more new lesions.

d. Blood drawn for serum PK measurements, immunogenicity assays (anti-M200 antibodies), vascular growth factors, and measurement of bound and unbound $\alpha 5\beta 1$ on peripheral blood monocytes.

e. A 3-mm punch biopsy of superficial tumor metastasis was obtained and frozen after the last treatment with M200 from patients who consented (not required for enrollment) to the procedure. This biopsy specimen could be used evaluate tumor vessel vascularity following treatment with M200.

5. Pharmacokinetic Measurements

The first human PK data at low doses was used to predict the human serum levels at higher doses (described above). The serum for measuring M200 concentrations was obtained immediately before and after the first dose, and at 4, 24, 48, and 168 hours after completion of the first dose. Serum samples for measuring M200 concentrations were also taken immediately before, at the end, and 4 hours after the completion of each subsequent infusion. These samples were split and aliquots assayed before the next dose and again at the end of the study: end of $1^{st}$ dose, 168 hours after $1^{st}$ dose, immediately pre-dose (trough) and immediately post-dose (peak) for the $2^{nd}$, $3^{rd}$, $4^{th}$ and $5^{th}$ doses. The serum levels of M200 were measured by ELISA.

The plasma concentration-time data of M200 from each patient was subjected to a PK analysis. The following parameters were included in the calculations: peak (Cmax) and trough (Cmin) levels, terminal phase half-life ($T_{1/2 \beta}$), area under the plasma-concentration time curve (AUC), elimination clearance (CL), and volume of distribution (V). Summary parameters were computed across patients from each treatment group. Changes in the PK parameters as a function of dose and time were also evaluated.

6. Immunogenicity

Immunogenicity of M200 was determined by a double-antigen bridging ELISA assay. Serum samples for anti-M200 antibodies were obtained from patients before treatment, prior to the second dose, and at study exit, 45 days after the last dose of M200. In addition, serum for anti-M200 antibodies was drawn if the interval between doses was 22 weeks. Samples were stored and evaluated at the end of the study. Samples that tested positive for antibodies to M200 were re-assayed for neutralizing antibodies to M200. Patients with known exposure to murine or chimeric monoclonal antibodies were screened for the presence of anti-M200 antibodies prior to receiving the first dose of M200.

7. Flow Cytometry Analysis

The integrin α5β1 is also expressed on monocytes in the peripheral blood. To determine the dose at which the α5β1 sites on these circulating cells is saturated by M200, samples of peripheral blood were taken before the first dose on Study Day 1, Study Days 2 and 8, just before each subsequent dose, and on Study Day 43. The saturation of α5β1 sites on monocytes was determined by flow cytometry. The monocytes were identified by using antibodies to CD14. Bound M200 on the monocyte surface was detected by adding labeled anti-human IgG4. Unoccupied (free) α5β1 on the cells was detected by adding labeled IIA1. The percentages of monocytes and lymphocytes expressing α5β1 was also assessed.

C. Results—Dose Escalation Study

M200 was well tolerated by patients at doses up to 15 mg/kg and no dose-limiting M200 toxicities were observed. The overall response outcome for the study was: stable disease (SD) in 11 patients and progressive disease (PD) in 10 patients. Table 4 shows a breakdown of the response outcome by dosage and patient tumor type.

TABLE 4

Response Outcomes by Dosage and Tumor Type

| 0.5 mg/kg | 1.0 mg/kg | 2.5 mg/kg | 5.0 mg/kg | 10.0 mg/kg | 15.0 mg/kg |
|---|---|---|---|---|---|
| CRC (PD) | HCC (SD) | CRC (PD) | HCC (SD) | CRC (SD) | EC (PD) |
| | PC (SD) | NSCLC (SD) | EC (PD) | CRC (SD) | RCC (SD) |
| | | MEL Ocular (PD) | THY (PD) | PARO (SD) | PRO (PD) |
| | | | | BC (SD) | MEL (PD) |
| | | | | RCC (SD) | MEL (SD) |
| | | | | MEL (PD) | RCC (PD) |

Abbreviations: CRC = colorectal; MEL = melanoma; RCC = renal; EC = esophogeal; HCC = hepatocellular; NSCLC = lung; PRO = prostate; THY = thyroid; PC = pancreatic; PARO = parotid; BC = breast; SD = Stable Disease; PD = Progressive Disease Adverse events were generally mild to moderate in intensity and included fatigue, nausea, constipation, headache and anorexia. There were no severe or serious adverse events that were dose limiting or considered by investigators to be related to M200. Three patients at the 0.5 mg/kg and 1.0 mg/kg dose levels tested positive for anti-M200 antibodies, but there were no apparent associated adverse events. No patients in the higher dose cohorts tested positive for anti-M200. The one patient who received 0.5 mg/kg had fever after the first dose, which was recorded as an infusion reaction. The patient, however, did complete all 5 doses of M200 without subsequent episodes of fever or other signs of infusion reaction.

The study data indicated that M200 exhibits non-linear pharmacokinetics. Slower-clearance was observed at the higher concentrations with the $T_{1/2}$=15.7 days at the 10 mg/kg dosage level. In addition, The 10 mg/kg dosage resulted in monocyte saturation, and had a mean trough level of 82 μg/mL two weeks after the 1st dose, which is above the minimum effective in vitro concentration of 2-3 μg/mL.

D. Results—Extension Study

Six of the 11 patients exhibiting a stable disease response or better entered an extension study and continued dosing. As shown in Table 5, below, 5 of the 6 patients exhibited stable disease (SD) or better response. One of these patients with renal cell cancer (RCC) in the 15.0 mg/kg cohort achieved a partial response.

TABLE 5

Extension Study Outcomes

| Dose Cohort (# patients; tumor type) | Best Response Outcome | Time to Progression* (Days) |
|---|---|---|
| 2.5 mg/kg (1; NSCLC) | SD | 129 |
| 5 mg/kg (1; HCC) | SD | 122 |
| 10 mg/kg (1; CRC) | PD | 70 |
| 10 mg/kg (1; PARO) | SD | 143 |
| 15 mg/kg (1; RCC) | PR | 214 |
| 15 mg/kg (1; MEL) | SD | 172+ (on Study) |

*Includes 43 days on dose escalation study plus days on extension study.
SD defined as stabilization for ≧16 weeks (112 days)

Example 9

Phase II Open-Label Study of M200 in Human Patients with Metastatic Renal Cell Carcinoma A. Overview Based on the efficacy of M200 demonstrated by the Phase I study of Example 8, a Phase II, open-label, multi-center, single-arm, 2-stage study of the efficacy of M200 for treating human patients has been undertaken. The primary objective of the study is to evaluate the efficacy (tumor response) of M200 in patients with metastatic renal cell carcinoma (RCC), as defined using Response Criteria for Solid Tumors (see RECIST, Example 8 above). The study also has as secondary objectives evaluation of other efficacy measures (ie, time to disease progression and duration of response), and further evaluation of the safety, immunogenicity and PK parameters of M200 that were initially evaluated in the Phase I study of Example 8. An additional exploratory objective is to measure detectable biomarkers in serum and plasma. The study will enroll up to 40 patients at up to eight investigational sites. Twenty patients will be enrolled into stage one of the study. If one confirmed complete response (CR) or partial response (PR) is observed by 4 months (16 weeks) or if one stable disease (SD) is observed at 4 months, an additional 20 patients will be enrolled (stage 2). All patients will receive M200 (10 mg/kg) as an intravenous infusion over 30 minutes once every other week for up to 52 weeks or until disease progression, whichever occurs first. The study exit visit will occur 45 days after the last dose or at the time of early termination if the patient is unable to return. A follow-up visit will occur at 3 months after the last dose. If a visit is not feasible, follow-up will be conducted by telephone. Long-term follow-up will be conducted by telephone at 6 months after the last dose.

B. Study Parameters and Protocols

The Phase II study is being conducted according to the parameters and protocols described in Table 6 below.

TABLE 6

| Parameters of Phase II Study in Patients with Metastatic Renal Cell Carcinoma | |
|---|---|
| Study Population: | Males and females of at least 18 years of age with metastatic RCC of clear cell histology. |
| Key Patient Inclusion/Exclusion Criteria: | Inclusion: Males and females of at least 18 years of age with metastatic RCC of predominantly clear cell histology who have received 0 to 2 prior regimens for metastatic disease; measurable disease according to Response Criteria for Solid Tumors (RECIST); Eastern Cooperative Oncology Group (ECOG) performance status $\leq 1$; negative pregnancy test (women of childbearing potential only); pretreatment laboratory levels that meet specific criteria; and signed informed consent, including permission to use protected health information (PHI). Exclusion: Any of the following histologies of RCC: papillary, chromophobe, collecting duct, or unclassified; known sensitivity to murine proteins or chimeric antibodies or other components of the product; use of any investigational drug within 4 weeks prior to screening or 5 half-lives of the prior investigational drug (whichever is longer); systemic chemotherapy, immunotherapy, radiation therapy, or monoclonal antibody therapy within 4 weeks of M200 administration; documented CNS tumor or CNS metastasis; history of thromboembolic events and bleeding disorders within the past year; and medical conditions that may be exacerbated by bleeding. |
| Sample Size: | Up to 40 patients may be enrolled. Twenty patients will be enrolled into stage one. If one confirmed complete response (CR) or partial response (PR) is observed by 4 months (16 weeks) or if one stable disease (SD) is observed at 4 months, an additional 20 patients will be enrolled (stage 2). |
| Dosage Form and Strength/Formulation: | M200 is a sterile, colorless, clear-to-slightly opalescent, preservative-free liquid for IV use. Each 10-mL single-use vial is filled to deliver 10 mL of M200 at 10 mg/mL. The composition of each vial is 10 mg/mL M200, 25 mM citrate, 150 mM sodium chloride, and 0.05% Polysorbate (Tween ®) 80, with a pH of 6.5. |
| Storage and Filtration: | Intact vials will be stored in a refrigerator at 2° C. to 8° C. (36° F. to 46° F.). Do not freeze or shake. M200 must be administered within 6 hours if stored at room temperature (25° C.) or 48 hours if refrigerated (between 2° C. to 8° C.). After that time, the prepared solution must be discarded. |
| Dosing Regimen/Route of Administration: | All eligible patients will receive 10 mg/kg M200 by intravenous (IV) infusion over 30 minutes every other week for up to 52 weeks or until disease progression, whichever occurs first. The dose of M200 to be administered to the patient will be calculated by multiplying the patient's weight (kg) by the dose level (10 mg/kg). The patient's predose weight on Study Day 0 will be used to calculate the dose throughout the study, provided the weight does not vary by more than 10%. The appropriate volume of the 10 mg/mL M200 formulation will be removed and diluted with 0.9% sodium chloride to a final volume of 120 mL for IV infusion into the patient over the 30 minute period. |
| Duration of Treatment and Follow-up: | All patients will receive M200 (10 mg/kg) intravenously once every other week for up to 52 weeks or until disease progression, whichever occurs first. The study exit visit will occur 45 days after the last dose or at the time of early termination if the patient is unable to return. A follow-up visit will occur at 3 months after the last dose. If a visit is not feasible, follow-up will be conducted by telephone. Long-term follow-up will be conducted by telephone at 6 months after the last dose. |
| Endpoints: | The primary endpoint of this study is the proportion of patients with a confirmed tumor response at any time during the study. The secondary endpoints are as follows: (1) time to disease progression; (2) duration of tumor response; (3) PK of M200; and (4) immunogenicity. The exploratory endpoint is the measurement of detectable biomarkers in serum and plasma. |
| Efficacy Measurements: | Disease-directed radiographic imaging every 8 weeks (2 months) to evaluate tumor response using uni-dimensional RECIST. At screen, CT or MRI of the head, chest, abdomen, and pelvis will be obtained. Every 8 weeks, a complete physical examination and imaging scans of all lesions present at screen plus all disease- |

TABLE 6-continued

Parameters of Phase II Study in Patients with Metastatic Renal Cell Carcinoma

| | |
|---|---|
| | directed anatomical lesions will be performed. For any PR or CR, confirmatory radiographic imaging will be repeated one month (between 28 to 35 days) post-PR or -CR. All measurable lesions up to a maximum of 5 lesions per organ and 10 lesions in total, representative of all involved organs, should be identified as target lesions and will be recorded and measured at baseline. Measurable lesions are defined as follows: 2.0 cm in one dimension using conventional CT/MRI and 1.0 cm in one dimension using spiral CT. A sum of the longest diameter (LD) for all target lesions will be calculated and reported as the baseline sum LD. The baseline sum LD will be used as the reference by which objective tumor response will be characterized. |
| Safety Measurements: | The following safety measurements will be monitored: adverse events (AE); serious adverse events (SAE); physical examination findings; vital signs; and abnormal laboratory values. |
| Pharmacokinetic Measurements: | Pharmacokinetic (PK) measurements will be taken in all patients at predose (within 15 minutes prior to dosing) and postdose (one hour post-end of infusion): Day 0, Weeks 2, 4, and 6, once every other month (Weeks 8, 16, 24, 32, 40, 48), Week 52, study exit visit, and 3-month follow-up (if possible). Samples obtained for PK may be used for anti-Ab analyses, if appropriate. |
| Immunogenicity: | Anti-Ab measurements will be taken in all patients within 15 minutes prior to dosing on Day 0, Week 8, study exit visit, and 3-month follow-up (if possible). Samples obtained for PK may be used for anti-Ab analyses, if appropriate. |
| Other Measurements: | An exploratory assay will evaluate the presence of biomarkers in serum and plasma. The following cancer markers are included in the assay: CEA, CA 19-9, Syndecan, IGFBP-2, and LFL2. The following cytokines/growth factors are included: MIA, IL-6, TNF-alpha, PGF, VEGF, EGF, and bFGF. |
| Statistical Methods: | This study design will yield a power of at least 79.5% for detecting an overall response rate of ≧20% with up to 20% of the responders displaying stable disease (SD). Summary statistics and 95% confidence intervals will be provided for dichotomous endpoints. Kaplan-Meier methods will be used to summarize temporal variables. |

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

---

We claim:

1. A pharmaceutical composition comprising a liquid formulation comprising:
    about 1.0 mg/mL to 15 mg/mL anti-α5β1 antibody;
    about 22 mM to 27 mM citrate;
    about 145 mM to 165 mM sodium chloride;
    about 0.04% to 0.06% polysorbate-80;
    and a pH of about 5.5 to 7.5.

2. The pharmaceutical composition of claim 1, wherein the concentration of anti-α5β1 antibody is about 10 mg/mL.

3. The pharmaceutical composition of claim 1, wherein the anti-α5β1 antibody comprises a heavy chain variable sequence of SEQ ID NO: 6 and a light chain variable sequence of SEQ ID NO: 8.

4. The pharmaceutical composition of claim 3, wherein the anti-α5β1 antibody comprises a Fab fragment of the antibody of claim 3.

5. The pharmaceutical composition of claim 1, wherein the composition further comprises a chemotherapeutic agent.

6. The pharmaceutical composition of claim 3, wherein the pH is about 6.3-6.7.

7. The pharmaceutical composition of claim 1, wherein the antibody comprises CDR sequences present in the antibody comprising a heavy chain variable sequence of SEQ ID NO: 2 and a light chain variable sequence of SEQ ID NO: 4 and a human IgG constant region.

8. The pharmaceutical composition of claim 7, wherein the human IgG constant region is IgG4.

9. A pharmaceutical composition comprising a liquid formulation comprising:
- about 10 mg/mL anti-α5β1 antibody;
- about 25 mM citrate;
- about 150 mM sodium chloride;
- about 0.05% polysorbate-80;
- and a pH of about 6.5.

10. The pharmaceutical composition of claim 9, wherein the antibody comprises CDR sequences present in the antibody comprising a heavy chain variable sequence of SEQ ID NO: 6 and a light chain variable sequence of SEQ ID NO: 8 and a human IgG constant region.

11. The pharmaceutical composition of claim 10, wherein the human IgG constant region is IgG4.

12. The pharmaceutical composition of claim 11, wherein the anti-α5β1 antibody comprises a heavy chain variable sequence of SEQ ID NO: 6 and a light chain variable sequence of SEQ ID NO: 8.

13. A pharmaceutical composition comprising a liquid formulation comprising:
- about 10 mg/mL anti-α5β1 antibody;
- about 22 mM to 27 mM citrate;
- about 145 mM to 165 mM sodium chloride;
- about 0.04% to 0.06% polysorbate-80;
- and a pH of about 6.5.

* * * * *

SEQUENCE LISTING

```
<160> NUMBER OF SEQ ID NOS: 8

<210> SEQ ID NO 1
<211> LENGTH: 429
<212> TYPE: DNA
<213> ORGANISM: mus muscalus

<400> SEQUENCE: 1
atggctgtcc tggggctgct tctctgcctg gtgactttcc caagctgtgt cctgtcccag      60
gtgcagctga aggagtcagg acctggcctg gtggcgccct cacagagcct gtccatcaca     120
tgcaccatct cagggttctc attaaccgac tatggtgttc actgggttcg ccagcctcca     180
ggaaagggtc tggagtggct ggtagtgatt tggagtgatg gaagctcaac ctataattca     240
gctctcaaat ccagaatgac catcaggaag gacaactcca agagccaagt tttcttaata     300
atgaacagtc tccaaactga tgactcagcc atgtactact gtgccagaca tggaacttac     360
tacggtatga ctacgacggg ggatgctttg gactactggg gtcaaggaac ctcagtcacc     420
gtctcctca                                                             429
```

```
<210> SEQ ID NO 2
<211> LENGTH: 143
<212> TYPE: PRT
<213> ORGANISM: mus muscalus

<400> SEQUENCE: 2

Met Ala Val Leu Gly Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Ile Ser Gly Phe Ser Leu
        35                  40                  45

Thr Asp Tyr Gly Val His Trp Val Arg Gln Pro Pro Gly Lys Gly Leu
    50                  55                  60

Glu Trp Leu Val Val Ile Trp Ser Asp Gly Ser Thr Tyr Asn Ser
65                  70                  75                  80

Ala Leu Lys Ser Arg Met Thr Ile Arg Lys Asp Asn Ser Lys Ser Gln
                85                  90                  95

Val Phe Leu Ile Met Asn Ser Leu Gln Thr Asp Asp Ser Ala Met Tyr
            100                 105                 110

Tyr Cys Ala Arg His Gly Thr Tyr Tyr Gly Met Thr Thr Thr Gly Asp
        115                 120                 125

Ala Leu Asp Tyr Trp Gly Gln Gly Thr Ser Val Thr Val Ser Ser
    130                 135                 140

<210> SEQ ID NO 3
<211> LENGTH: 390
<212> TYPE: DNA
<213> ORGANISM: mus muscalus

<400> SEQUENCE: 3 atggatttc aggtgcagat tttcagcttc ctgctaatca gtgcctcagt cataatgtcc      60
agaggacaaa ttgttctcac ccagtctcca gcaatcatgt ctgcatctct aggggaacgg    120
gtcaccatga cctgcactgc cagttcaagt gtaagttcca attacttgca ctggtaccag    180
cagaagccag atccgcccc caatctctgg atttatagca catccaacct ggcttctgga    240
gtcccagctc gtttcagtgg cagtgggtct gggacctctt actctctcac aatcagcagc    300
atggaggctg aagatgctgc cacttattac tgccaccagt atcttcgttc cccaccgacg    360
ttcggtggag gcaccaagct ggaaatcaaa                                     390

<210> SEQ ID NO 4
<211> LENGTH: 130
<212> TYPE: PRT
<213> ORGANISM: mus muscalus

<400> SEQUENCE: 4

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Asn Tyr Leu His Trp Tyr Gln Gln Lys Pro Gly
    50                  55                  60

Ser Ala Pro Asn Leu Trp Ile Tyr Ser Thr Ser Asn Leu Ala Ser Gly
65                  70                  75                  80
```

```
Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr Leu Arg Ser Pro Pro Thr Phe Gly Gly Gly Thr Lys Leu Glu
        115                 120                 125

Ile Lys
    130

<210> SEQ ID NO 5
<211> LENGTH: 459
<212> TYPE: DNA
<213> ORGANISM: Artificial
<220> FEATURE:
<223> OTHER INFORMATION: chimeric antibody

<400> SEQUENCE: 5
tctagaccac catggctgtc ctggggctgc ttctctgcct ggtgactttc ccaagctgtg      60
tcctgtccca ggtgcagctg aaggagtcag acctggcct ggtggcgccc tcacagagcc     120
tgtccatcac atgcaccatc tcaggttct cattaaccga ctatggtgtt cactgggttc     180
gccagcctcc aggaaagggt ctggagtggc tggtagtgat ttggagtgat ggaagctcaa    240
cctataattc agctctcaaa tccagaatga ccatcaggaa ggacaactcc aagagccaag    300
ttttcttaat aatgaacagt ctccaaactg atgactcagc catgtactac tgtgccagac    360
atggaactta ctacggaatg actacgacgg gggatgcttt ggactactgg ggtcaaggaa    420
cctcagtcac cgtctcctca ggtaagaatg gcctctaga                           459

<210> SEQ ID NO 6
<211> LENGTH: 143
<212> TYPE: PRT
<213> ORGANISM: Artificial
<220> FEATURE:
<223> OTHER INFORMATION: chimeric antibody

<400> SEQUENCE: 6

Met Ala Val Leu Gly Leu Leu Leu Cys Leu Val Thr Phe Pro Ser Cys
1               5                  10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Ile Ser Gly Phe Ser Leu
        35                  40                  45

Thr Asp Tyr Gly Val His Trp Val Arg Gln Pro Pro Gly Lys Gly Leu
    50                  55                  60

Glu Trp Leu Val Val Ile Trp Ser Asp Gly Ser Ser Thr Tyr Asn Ser
65                  70                  75                  80

Ala Leu Lys Ser Arg Met Thr Ile Arg Lys Asp Asn Ser Lys Ser Gln
                85                  90                  95

Val Phe Leu Ile Met Asn Ser Leu Gln Thr Asp Asp Ser Ala Met Tyr
            100                 105                 110

Tyr Cys Ala Arg His Gly Thr Tyr Tyr Gly Met Thr Thr Gly Asp
        115                 120                 125

Ala Leu Asp Tyr Trp Gly Gln Gly Thr Ser Val Thr Val Ser Ser
    130                 135                 140

<210> SEQ ID NO 7
<211> LENGTH: 425
<212> TYPE: DNA
```

-continued

```
<213> ORGANISM: Artificial
<220> FEATURE:
<223> OTHER INFORMATION: chimeric antibody

<400> SEQUENCE: 7
acgcgtccac catggatttt caggtgcaga ttttcagctt cctgctaatc agtgcctcag      60
tcataatgtc cagaggacaa attgttctca cccagtctcc agcaatcatg tctgcatctc     120
taggggaacg ggtcaccatg acctgcactg ccagttcaag tgtcagttcc aattacttgc     180
actggtacca gcagaagcca ggatccgccc ccaatctctg gatttatagc acatccaacc     240
tggcttctgg agtcccagct cgtttcagtg gcagtgggtc tgggacctct tactctctca     300
caatcagcag catggaggct gaagatgctg ccacttatta ctgccaccag tatcttcgtt     360
ccccaccgac gttcggtgga ggcaccaagc tggaaatcaa acgtaagtag aatccaaagt     420
ctaga                                                                 425

<210> SEQ ID NO 8
<211> LENGTH: 138
<212> TYPE: PRT
<213> ORGANISM: Artificial
<220> FEATURE:
<223> OTHER INFORMATION: chimeric antibody

<400> SEQUENCE: 8
```

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Thr Met Thr Cys Thr Ala Ser
        35                  40                  45

Ser Ser Val Ser Ser Asn Tyr Leu His Trp Tyr Gln Gln Lys Pro Gly
    50                  55                  60

Ser Ala Pro Asn Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr Leu Arg Ser Pro Pro Thr Phe Gly Gly Gly Thr Lys Leu Glu
        115                 120                 125

Ile Lys Asp Met Ser Val Asp Met Ser Val
    130                 135